United States Patent
Cogan et al.

(10) Patent No.: US 7,511,042 B2
(45) Date of Patent: Mar. 31, 2009

(54) TRIAZOLE COMPOUNDS

(75) Inventors: Derek Cogan, Sandy Hook, CT (US);
Daniel R. Goldberg, Redding, CT (US);
Abdelhakim Hammach, Danbury, CT (US); Matthew Russell Netherton, Danbury, CT (US); Ronald A. Aungst, Clifton Park, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 545 days.

(21) Appl. No.: 11/002,022

(22) Filed: Dec. 1, 2004

(65) Prior Publication Data
US 2005/0153972 A1 Jul. 14, 2005

Related U.S. Application Data

(60) Provisional application No. 60/526,569, filed on Dec. 3, 2003.

(51) Int. Cl.
C07D 401/02 (2006.01)
A61K 31/44 (2006.01)

(52) U.S. Cl. .............. 514/252.05; 514/341; 514/359; 544/238; 546/268.1; 548/261

(58) Field of Classification Search .............. 544/238; 546/268.1; 548/261; 514/252.05, 341, 359
See application file for complete search history.

(56) References Cited

U.S. PATENT DOCUMENTS

| | | | |
|---|---|---|---|
| 6,455,520 B1 | 9/2002 | Brown et al. | |
| 7,166,628 B2 * | 1/2007 | Cogan et al. | 514/383 |
| 2005/0004176 A1 | 1/2005 | Dyckman et al. | |

FOREIGN PATENT DOCUMENTS

| | | |
|---|---|---|
| DE | 4302051 A1 | 7/1994 |
| EP | 0 051 084 A1 | 5/1982 |
| EP | 1 063 228 A1 | 12/2000 |
| WO | WO 96/32382 A1 | 10/1996 |
| WO | WO 99/51580 A1 | 10/1999 |
| WO | WO 00/24735 A1 | 5/2000 |
| WO | WO 01/68568 A2 | 9/2001 |
| WO | WO 01/72740 A1 | 10/2001 |
| WO | WO 03/002910 A1 | 1/2003 |
| WO | WO 03/022820 A1 | 3/2003 |
| WO | WO 03/030902 A1 | 4/2003 |
| WO | WO 03/063781 A2 | 8/2003 |
| WO | WO 2004/050642 A1 | 6/2004 |

OTHER PUBLICATIONS

International Search Report PCT/US2004/040306, Jan. 12, 2004, BI Pharmaceuticals, Inc.
English Translation for DE 43 02 051 A1.
Higham, M. A. et al; "Tumour necrosis factor-alpha gene promoter polymorphism in chronic obstructive pulmonary disease"; Eur. Respir J. 2000, 15:281-284.
Takabatake, N. et al; "The Relationship between Chronic Hypoxemia and Activation of the Tumor Necrosis Factor-alpha System in Patients with Chronic Obstructive Pulmonary Disease"; Am. J. Respir. Crit. Care Med., vol. 161, 2000, 1179-1184.
"Tumor Necrosis Factor Inhibitors"; Early Alert Report, Fall 2000.
van Heel, D. A et al; "Inflammatory bowel disease is associated with a TNF polymorphism that affects an interaction between the OCT1 and NF-kB transcription factors"; Human Molecular Genetics (2002): 1281-1289.
Raine, C. S. et al; "Multiple sclerosis: expression of molecules of the tumor necrosis factor ligand and receptor families in relationship to the demyelinated plaque"; Rev. Neurol. (Paris) 1998, 154, 577-585.
Chodorowska, C. et al; "Plasma concentrations of IFN-gamma and TNF-alpha in psoriatic patients before and after local treatment with dithranol ointment"; J. Eur. Acad. Dermatollogy And Venereology, 1998, 10, 147-151.
Robak, E., "Association of Interferon gamma, Tumor Necrosis Factor alpha and Interleukin 6 Serum Levels with Systemic Lupus Erythematosus Activity"; Archivum Immunologiae et Therapiae Experimentalis, 1998, 46, 375-380.

* cited by examiner

*Primary Examiner*—Zinna N Davis
(74) *Attorney, Agent, or Firm*—Michael P. Morris; Mary-Ellen M. Devlin; Anthony P. Bottino

(57) ABSTRACT

Disclosed are compounds of formula (I)

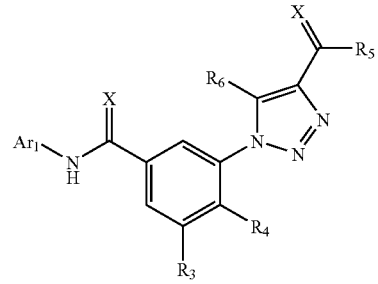

Where $Ar_1$, X, $R_3$, $R_4$, $R_5$ and $R_6$ are defined herein. The compounds of the invention inhibit production of cytokines and are thus useful for treating cytokine mediated diseases. Also disclosed are processes for preparing these compounds and pharmaceutical compositions comprising these compounds.

15 Claims, No Drawings

TRIAZOLE COMPOUNDS

APPLICATION DATA

This application claims benefit to U.S. provisional application No. 60/526,569 filed Dec. 3, 2003.

BACKGROUND OF THE INVENTION

1. Technical Field

This invention relates to compounds of formula (I)

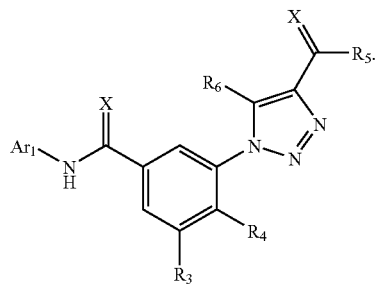

The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

2. Background Information

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6: 51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). Studies suggest that inflammatory changes mediated by cytokines may be involved in endothelial cell pathogenesis including restenosis after percutaneous transluminal coronary angioplasty (PTCA) (Tashiro, H., et al., 2001 March, *Coron Artery Dis* 12(2): 107-13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J Rheum.* 35: 334-342 and Stack, W. A., et al., 1997, *Lancet* 349: 521-524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143). IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242). TNFα levels are elevated in airways of patients with chronic obstructive pulmonary disease and it may contribute to the pathogenesis of this disease (M. A. Higham et al., 2000, *Eur. Respiratory J,* 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3-12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.,* 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFNγ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFNγ (Ablumunits, et al., 1998, *J Autoimmun.* 11, 73). IFNγ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFNγ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFNγ following challenge with Vespula venom (Bonay, et al., 1997, *Clin Exp Immunol.* 109, 342). The expression of a number of cytokines, including IFNγ has been shown to increase following a delayed type hypersensitivity reaction thus indicating a role for IFNγ in atopic dermatitis (Szepietowski, et al., 1997, *Br J Dermatol.* 137, 195). Histopathologic and immunohistologic studies were performed in cases of fatal cerebral malaria. Evidence for elevated IFNγ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFNγ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFNγ, TNF and IL-2 (Chisari, et al., 1995, *Springer Semin Immunopathol.* 17, 261). IFNγ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFNγ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFNγ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). An elevated level of serum IgE is associated with various atopic diseases such as bronchial asthma and atopic dermatitis. The level of IFNγ was negatively correlated with serum IgE suggesting a role for IFNγ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα antagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95-101; Shock 1998 Sep. 10(3): 160-75. p38MAP kinase pathway plays an role in B.burgdorferi-elicited inflammation and may be useful in treating inflammation induced by the Lyme disease agent. Anguita, J. et. al., *The Journal of Immunology,* 2002, 168: 6352-6357. There is also increased evidence for a supporting role for MAPK signaling in antitumor drug action, MAPK modulators may have potential as chemotherapeutic drugs themselves or as chemosensitizing agents. Fan MY. Et. al., *Drug Resistance Updates.* 2001 August, 4(4): 253-267.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with small molecule compounds will be beneficial in the treatment of various disease states.

It is therefore an object of the invention to provide compounds of formula (I)

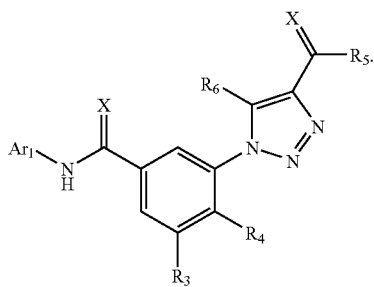

It is a further object of the invention to provide methods for treating cytokine mediated diseases and pathological conditions involving inflammation such as chronic inflammatory disease, using the novel compounds of the invention.

It is yet a further object of the invention to provide pharmaceutical compositions and processes of preparation of the above-mentioned novel compounds.

DETAILED DESCRIPTION OF THE INVENTION

In the broadest generic embodiment, there is provided compounds of the formula (I)

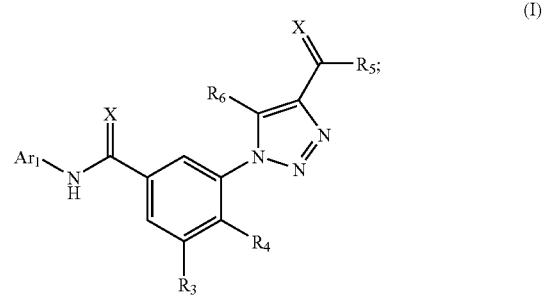

wherein:
$Ar_1$ is chosen from rings (i), (ii) or (iii) below:

wherein one of A or B is nitrogen and the other is carbon, $R_1$ is covalently attached to either A or B, and when nitrogen is N—$R_1$ the double bond between A and B is not present;
$R_1$ is hydrogen, $NO_2$, —$N(R^c)_2$, J-C(O)— $N(R^c)$— or J-S(O)$_m$— $N(R^c)$—;
or $R_1$ is chosen from $C_{1-6}$ alkyl, $C_{3-7}$ cylcoalkyl, $C_{1-5}$ alkoxyl or $C_{3-7}$ cycloalkoxyl, $C_{1-5}$ alkylthiol or $C_{3-7}$ cycloalkylthiol, $C_{1-5}$ acyl, $C_{1-5}$ alkoxycarbonyl, $C_{1-5}$ acyloxy, $C_{1-5}$ acylamino, $C_{2-5}$ alkenyl, $C_{2-5}$ alkynyl, heterocycle, heteroaryl, or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;
$R_2$ is chosen from hydrogen, halogen, $C_{1-5}$ alkyl, $C_{1-5}$ alkoxy, $C_{1-5}$ alkylC$_{1-5}$ alkoxy, hydroxy, hydroxy $C_{1-5}$ alkyl, oxo, $C_{1-5}$ alkylS(O)$_m$—, or amino optionally mono- or di-substituted by $C_{1-5}$ alkyl, aryl or aryl $C_{1-5}$ alkyl;

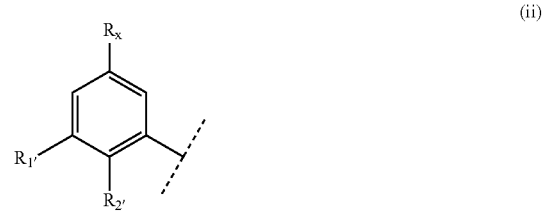

wherein
$R_1'$ is chosen from H, $C_{1-5}$ alkylS(O)$_m$—, $C_{1-6}$ alkyl, $C_{3-7}$ cylcoalkyl, $C_{1-5}$ alkoxyl or $C_{3-7}$ cycloalkoxyl, $C_{1-5}$ alkylthiol $C_{3-7}$ cycloalkylthiol, $C_{1-5}$ acyl, $C_{1-5}$ alkoxycarbonyl, $C_{1-5}$ acyloxy, $C_{2-5}$ alkenyl, $C_{2-5}$ alkynyl, heterocycle, heterocycleC$_{1-6}$ alkyl, heteroaryl, heteroarylC$_{1-6}$ alkyl, or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;

$R_2'$ is chosen from nitrile, C1-5 alkylS(O)$_m$—, J-O—C(O)—O—, $NH_2$—C(O)—$(CH_2)_n$—, hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl or amino optionally mono- or di-substituted by $C_{1-5}$ alkyl, aryl or aryl $C_{1-5}$ alkyl;

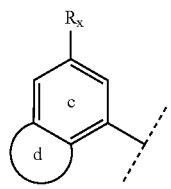

(iii)

wherein c is a benzo ring fused to ring d which is a 5-7 membered heterocyclic ring;

each $R_x$ is chosen from $C_{1-6}$ alkyl or $C_{3-7}$ cycloalkyl each being optionally substituted by $C_{1-3}$ alkyl and optionally partially or fully halogenated, $C_{1-4}$ acyl, aroyl, $C_{1-4}$ alkoxy, which may optionally be partially or fully halogenated, halogen, $C_{1-6}$ alkoxycarbonyl, carbocyclesulfonyl and —$SO_2$—$CF_3$;

m and n are 0, 1 or 2 and wherein $R^c$ is chosen from hydrogen or $C_{1-5}$ alkyl;

J is chosen from $C_{1-10}$ alkyl and carbocycle each optionally substituted by $R^b$;

$R_3$, $R_4$, $R_6$, $R_7$ and $R_8$ are each independently chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl or amino optionally mono- or di-substituted by $C_{1-5}$ alkyl, aryl or aryl $C_{1-5}$ alkyl;

$R_5$ is: a bond, —O—, —S—, —N<, —NH—, C(O), a linear chain chosen from —NH(CR$_7$R$_8$)$_r$—, —(CR$_7$R$_8$)$_r$—, —O(CR$_7$R$_8$)$_r$—, —C(O)—O(CR$_7$R$_8$)$_r$—, —S(CR$_7$R$_8$)$_r$—, C(O)(CR$_7$R$_8$)$_r$— and —C(O)NH(CR$_7$R$_8$)$_r$—, wherein r is 1-5 and each of the aforementioned $R_5$ is further substituted by $R^a$, or $R_5$ is a ring system chosen from aryl, heteroaryl or heterocyclyl each optionally substituted by $R^a$;

$R^a$ and $R^b$ are each independently chosen from hydrogen, $C_{1-5}$ alkyl, hydroxy$C_{1-5}$ alkyl, $C_{2-5}$ alkenyl, $C_{2-5}$ alkynyl, carbocycle, heterocycle, heteroaryl, $C_{1-5}$ alkoxy, $C_{1-5}$ alkylthio, amino, $C_{1-5}$ alkylamino, $C_{1-5}$ dialkylamino, $C_{1-5}$ acyl, $C_{1-5}$ alkoxycarbonyl, $C_{1-5}$ acyloxy, $C_{1-5}$ acylamino, each of the aforementioned are optionally partially or fully halogenated, or $R^a$ and $R^b$ are chosen from $C_{1-5}$ alkylsulphonylamino, hydroxy, oxo, halogen, nitro and nitrile, and X is O or S or the pharmaceutically acceptable salts, acids, esters or isomers thereof.

In another embodiment, there are provided compounds of the formula (I) as described above and wherein
if $Ar_1$ is (i) then:
$R_1$ is chosen from hydrogen, $C_{1-6}$ alkyl, $C_{3-7}$ cylcoalkyl, $C_{1-5}$ alkoxyl or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;

$R_2$ is chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl, oxo, C1-5 alkylS(O)$_m$—, or amino optionally mono- or di-substituted by $C_{1-5}$ alkyl, phenyl or phenyl $C_{1-5}$ alkyl;

if $Ar_1$ is (ii) then:
$R^{1'}$ is chosen from H, $C_{1-6}$ alkyl, $C_{1-5}$ alkylS(O)$_m$—, $C_{1-5}$ alkoxyl $C_{1-5}$ alkylthio, $NH_2$—C(O)—$(CH_2)_n$—, heterocycle, heterocycle$C_{1-6}$ alkyl, heteroaryl, or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;

$R_{2'}$ is chosen from $C_{1-5}$ alkylS(O)$_m$—, J-O—C(O)—O—, $C_{1-5}$ alkyl, $C_{1-5}$ alkoxy;

or if $Ar_1$ is (iii) then:
ring d is a 5-6 membered heterocyclic ring.

In another embodiment, there are provided compounds of the formula (I) as described above and wherein
if $Ar_1$ is (i) then:
$R_1$ is chosen from hydrogen, $C_{1-6}$ alkyl or nitrile;
$R_2$ is chosen from hydrogen, halogen, $C_{1-5}$ alkyl, $C_{1-5}$ alkoxy, oxo or $C_{1-5}$ alkylS(O)$_m$—,
if $Ar_1$ is (ii) then:
$R^{1'}$ is chosen from H, $C_{1-6}$ alkyl, $C_{1-5}$ alkylS(O)$_m$—, $C_{1-5}$ alkoxyl $C_{1-5}$ alkylthio, $NH_2$—C(O)—(CH2)$_n$—, morpholino $C_{1-6}$ alkyl, heteroaryl chosen from pyrazole, triazole, imidazole and tetrazole, and nitrile;
$R_2'$ is chosen from $C_{1-5}$ alkylS(O)$_m$—, J-O—C(O)—O—, $C_{1-5}$ alkyl, $C_{1-5}$ alkoxy;
or if $Ar_1$ is (iii) then:
ring d is a 5-6 membered heterocyclic ring such that rings c and d fuse to form the following:

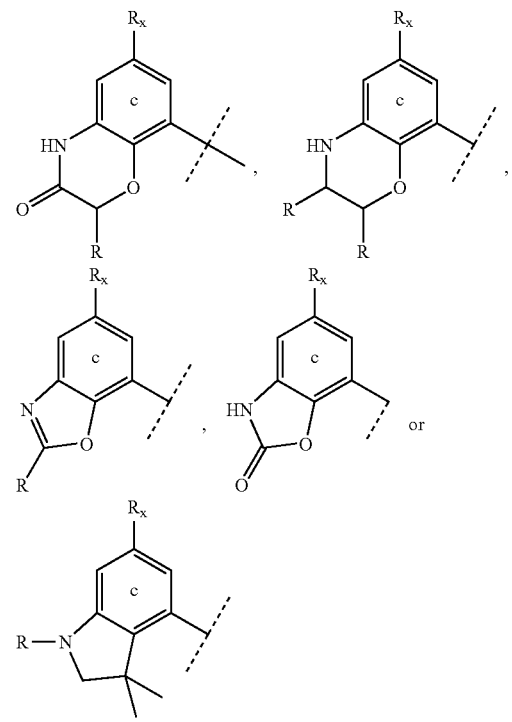

where R is H or $C_{1-3}$ alkyl;

In yet another embodiment, there are provided compounds of the formula (I) as described in any of the embodiments shown above and wherein J is chosen from C1-10 alkyl, aryl or C3-7 cycloalkyl each optionally substituted by $R^b$;

$R_x$ is independently chosen from C1-6 alkyl which may optionally be partially or fully halogenated, acetyl, aroyl, C1-4 alkoxy, which may optionally be partially or fully halogenated, halogen, methoxycarbonyl, phenylsulfonyl and —SO$_2$—CF$_3$;

r is 1-4;

$R^a$ and $R^b$ are each independently chosen from hydrogen, C1-5 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, C1-5 sulphonylamino, hydroxy, halogen, trifluoromethyl, nitro, nitrile or $R^a$ and $R^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl;

$R_7$ is hydrogen;

and X is O.

In yet another embodiment, there are provided compounds of the formula (I) as described immediately above and wherein $R_5$ is: —O—, —S—, —NH—, C(O), a linear chain chosen from —NH(CR$_7$R$_8$)$_r$—, —(CR$_7$R$_8$)$_r$—, —O(CR$_7$R$_8$)$_r$—, —C(O)—O(CR$_7$R$_8$)$_r$—, —S(CR$_7$R$_8$)$_r$—, C(O)(CR$_7$R$_8$)$_r$— and —C(O)NH(CR$_7$R$_8$)$_r$—, wherein r is 1-3 and each of the aforementioned $R_5$ is further substituted by $R^a$.

In yet another embodiment, there are provided compounds of the formula (I) as described immediately above and wherein J is C1-10 alkyl;

$R_x$ is independently chosen from $C_{1-6}$ alkyl which may optionally be partially or fully halogenated and $C_{1-3}$ alkoxy, which may optionally be partially or fully halogenated;

$R_3$ and $R_4$ are each independently chosen from hydrogen, $C_{1-3}$ alkyl and chloro;

$R_6$ is chosen from hydrogen and amino;

$R_5$ is: —NH—, C(O), a linear chain chosen from —NH(CR$_7$R$_8$)$_r$—, —(CR$_7$R$_8$)$_r$—, —O(CR$_7$R$_8$), —, —C(O)—O(CR$_7$R$_8$)$_r$—, C(O) (CR$_7$R$_8$)$_r$— and —C(O)NH(CR$_7$R$_8$)$_r$— wherein r is 1-2 and each of the aforementioned $R_5$ is further substituted by $R^a$, $R^a$ and $R^b$ are each independently chosen from hydrogen, C1-5 alkyl, C3-7 cycloalkylC0-2 alkyl, aryl, C1-5 alkoxy, amino, C1-5 alkylamino, C1-3 dialkylamino, C1-3 acyl, C1-5 alkoxycarbonyl, C1-3 acyloxy, C1-3 acylamino, C1-3 sulphonylamino, hydroxy, halogen, trifluoromethyl, nitro, nitrile;

or $R^a$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl.

In yet still another embodiment, there are provided compounds of the formula (I) as described immediately above and wherein J is C1-5 alkyl;

$R_x$ is independently chosen from C1-5 alkyl which may optionally be partially or fully halogenated and C1-2 alkoxy, which may optionally be partially or fully halogenated;

$R_3$ is hydrogen;

$R_4$ is chosen from hydrogen and methyl;

$R_8$ is hydrogen, methyl, ethyl, CH$_2$OH and CH$_2$OCH$_3$.

In yet another embodiment, there are provided compounds of the formula (I) as described immediately above and wherein $R_3$ is hydrogen;

$R_4$ is methyl;

$R^a$ is chosen from hydrogen, C1-5 alkyl, C3-6 cycloalkylC0-2 alkyl, phenyl, C1-5 alkoxy, amino, C1-5 alkylamino, C1-3 dialkylamino, C1-3 acyl, C1-5 alkoxycarbonyl, C1-3 acyloxy, C1-3 acylamino, hydroxy, halogen;

or $R^a$ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl.

In yet another embodiment, there are provided compounds of the formula (I) as described immediately above and wherein $R^a$ is chosen from hydrogen, C1-5 alkyl, C3-6 cycloalkyl, phenyl, C1-5 alkoxy, C1-5 alkoxycarbonyl, C1-3 acyloxy, C1-3 acylamino, hydroxy, halogen;

or $R^a$ is chosen morpholinyl, piperidinyl and pyridinyl.

In yet another embodiment, there are provided compounds of the formula (I) as described immediately above and wherein $R_5$ is —NH(CR$_7$R$_8$)$_r$—R$^a$, wherein R$^a$ is chosen from phenyl, morpholinyl, piperidinyl, pyridinyl, cyclopropyl, cyclohexyl, C1-5 alkyl and C1-3 alkoxy.

Preferred embodiments where $Ar_1$ is (i) include:

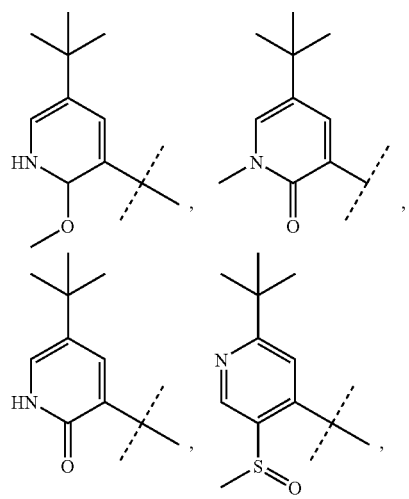

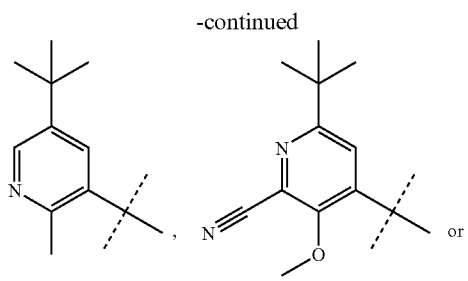
Preferred embodiments where Ar₁ is (ii) include:
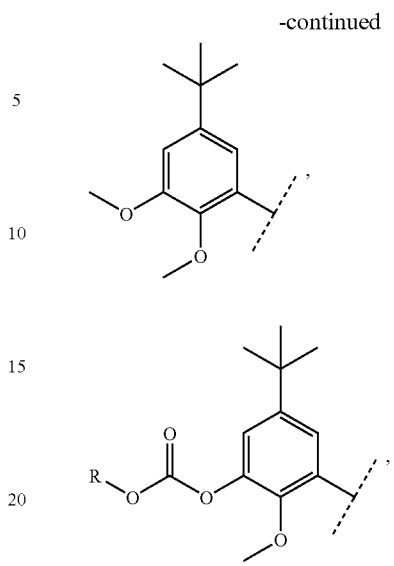
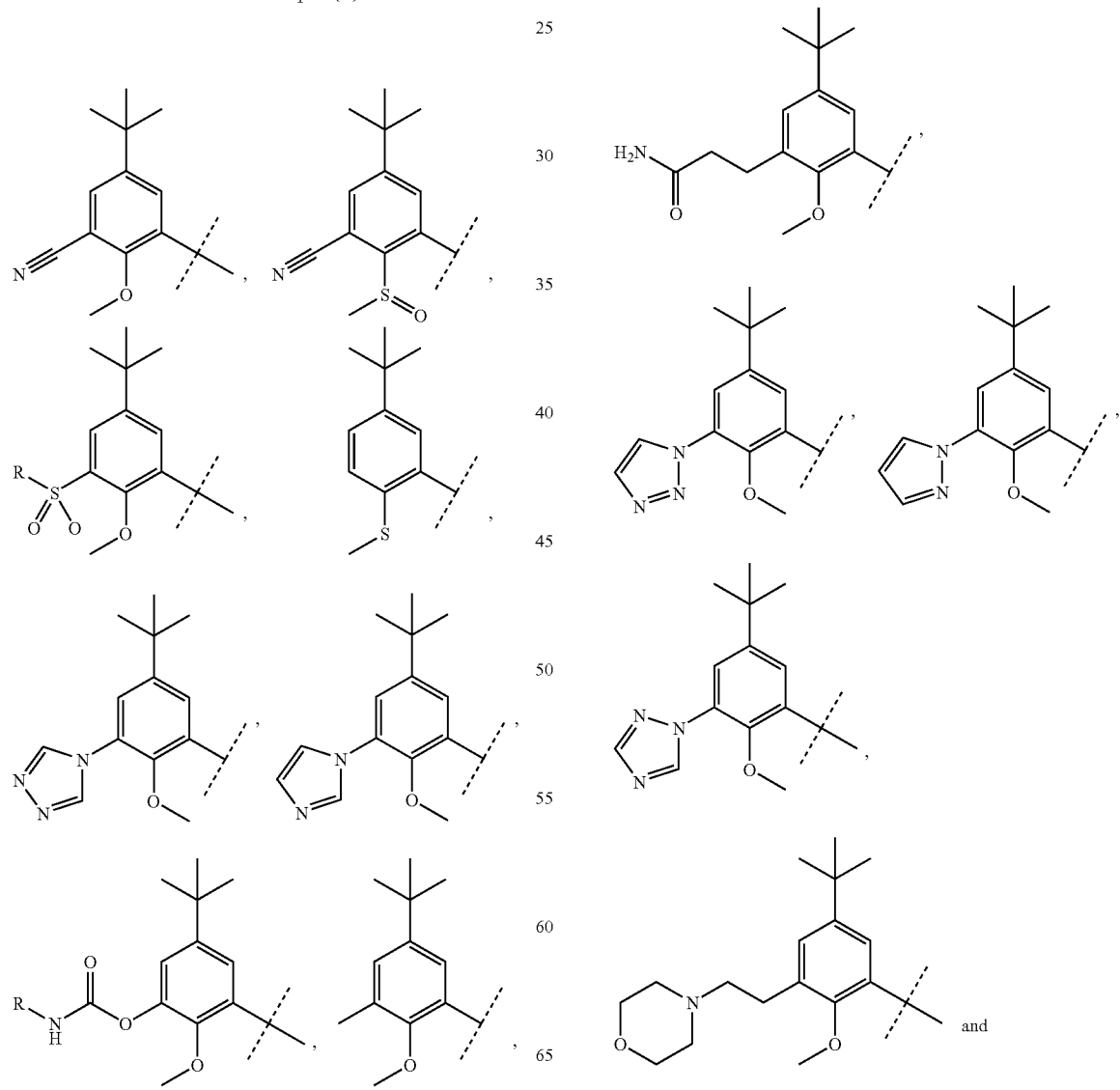
and -continued

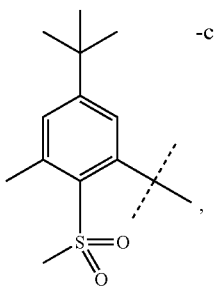

where R is as hereinabove defined.

The following are representative compounds of the invention which can be made according to the general schemes and working examples below:

TABLE I

| | |
|---|---|
| | 1-[5-(5-tert-Butyl-2-methoxy-3-methylsulfamoyl-phenylcarbamoyl)-2-methyl-phenyl]-1H-1,2,3-triazole-4-carboxylic acid (2,2-dimethyl-propyl)-amide |
| | 1-[5-(5-tert-Butyl-3-1,3-dioxolan-2-yl-2-methoxy-phenylcarbamoyl)-2-methyl-phenyl]-1H-1,2,3-triazole-4-carboxylic acid (2,2-dimethyl-propyl)-amide |
| | 1-[5-(5-tert-Butyl-3-dimethylaminomethyl-2-methoxy-phenylcarbamoyl)-2-methyl-phenyl]-1H-1,2,3-trizazole-4-carboxylic acid (2,2-dimethyl-propyl)-amide |
| | 1-{5-[5-tert-Butyl-2-methoxy-3-(3-methyl-piperazin-1-ylmethyl)-phenylcarbamoyl]-2-methyl-phenyl}-1H-1,2,3-triazole-4-carboxylic acid (2,2-dimethyl-propyl)-amide |

TABLE I-continued

| | |
|---|---|
| 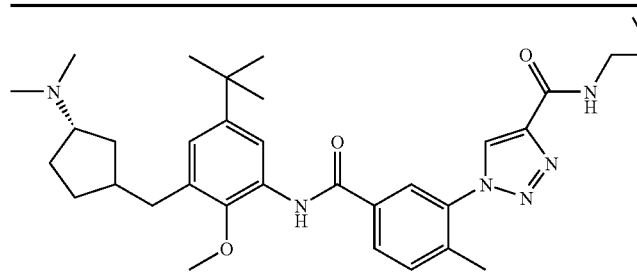 | 1-{5-[5-tert-Butyl-3-((S)-3-dimethylamino-pyrrolidin-1-ylmethyl)-2-methoxy-phenylcarbamoyl]-2-methyl-phenyl}-1H-1,2,3-triazole-4-carboxylic acid (2,2-dimethyl-propyl)-amide |
| 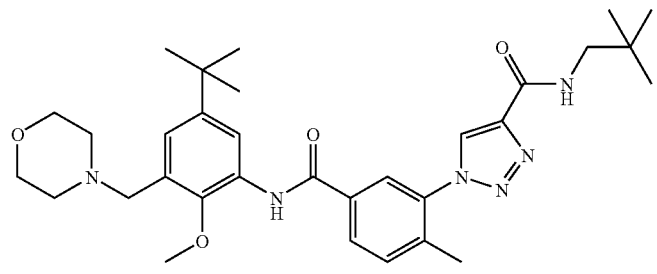 | 1-[5-(5-tert-Butyl-2-methoxy-3-morpholin-4-ylmethyl-phenylcarbamoyl)-2-methyl-phenyl]-1H-1,2,3-triazole-4-carboxylic acid (2,2-dimethyl-propyl)-amide |
| 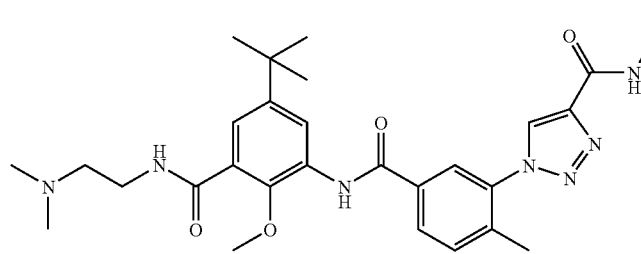 | 1-{5-[5-tert-Butyl-3-(2-dimethylamino-ethylcarbamoyl)-2-methoxy-phenylcarbamoyl]-2-methyl-phenyl}-1H-1,2,3-triazole-4-carboxylic acid (2,2-dimethyl-propyl)-amide |
| 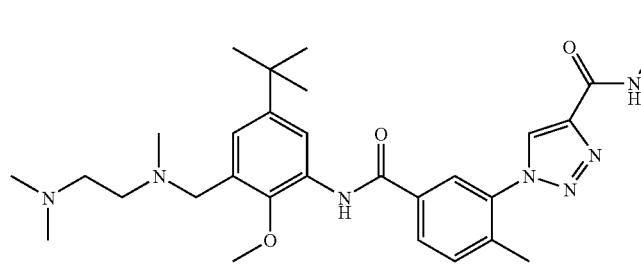 | 1-[5-(5-tert-Butyl-3-{[(2-dimethylamino-ethyl)-methyl-amino]-methyl}-2-methoxy-phenylcarbamoyl)-2-methyl-phenyl]-1H-1,2,3-triazole-4-carboxylic acid (2,2-dimethyl-propyl)-amide |
| 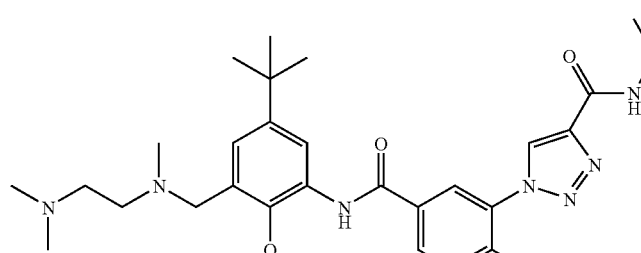 | 1-[5-(5-tert-Butyl-3-{[(2-dimethylamino-ethyl)-methyl-amino]-methyl}-2-methoxy-phenylcarbamoyl)-2-methyl-phenyl]-1H-1,2,3-triazole-4-carboxylic acid ((R)-1-phenyl-ethyl)-amide |
| 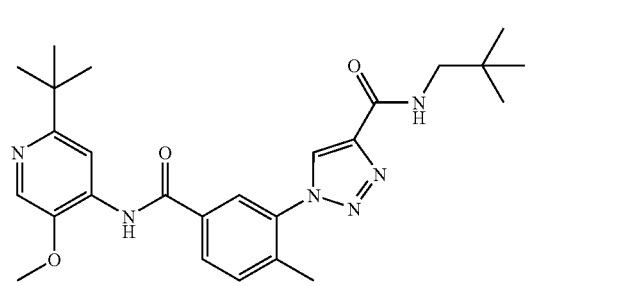 | 1-[5-(2-tert-Butyl-5-methoxy-pyridin-4-ylcarbamoyl)-2-methyl-phenyl]-1H-1,2,3-triazole-4-carboxylic acid (2,2-dimethyl-propyl)-amide |

TABLE I-continued

| | |
|---|---|
| 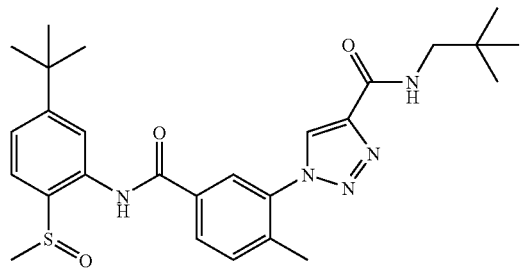 | 1-[5-(5-tert-Butyl-2-methanesulfinyl-phenylcarbamoyl)-2-methyl-phenyl]-1H-1,2,3-triazole-4-carboxylic acid (2,2-dimethyl-propyl)-amide | or the pharmaceutically acceptable salts, acids, esters or isomers thereof.

In addition to the abovementioned compounds, the following compounds of the formula (I) may be made by the general methods described in the specification:

TABLE II

| | |
|---|---|
| 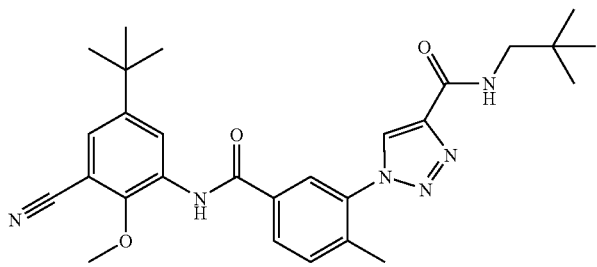 | 1-[5-(5-tert-Butyl-3-cyano-2-methoxy-phenylcarbamoyl)-2-methyl-phenyl]-1H-[1,2,3]triazole-4-carboxylic acid (2,2-dimethyl-propyl)-amide |
| 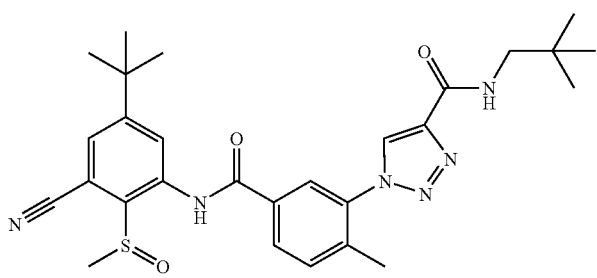 | 1-[5-(5-tert-Butyl-3-cyano-2-methanesulfinyl-phenylcarbamoyl)-2-methyl-phenyl]-1H-[1,2,3]triazole-4-carboxylic acid (2,2-dimethyl-propyl)-amide |
| 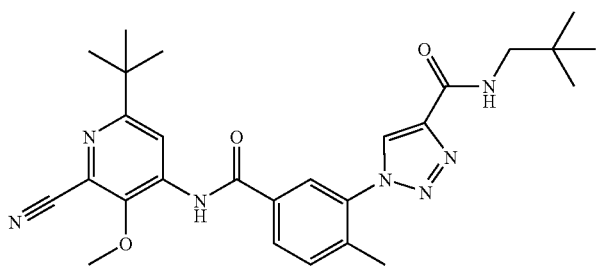 | 1-[5-(6-tert-Butyl-2-cyano-3-methoxy-pyridin-4-ylcarbamoyl)-2-methyl-phenyl]-1H-[1,2,3]triazole-4-carboxylic acid (2,2-dimethyl-propyl)-amide |

TABLE II-continued

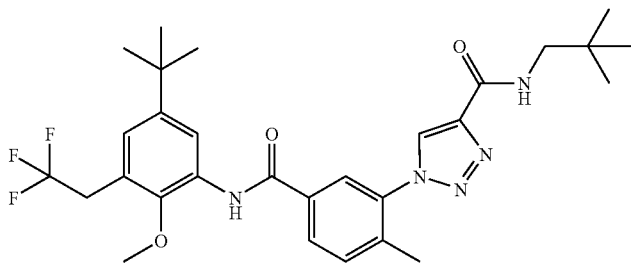

1-[5-(5-tert-Butyl-2-methoxy-3-trifluoromethanesulfonyl-phenylcarbamoyl)-2-methyl-phenyl]-1H-[1,2,3]triazole-4-carboxylic acid (2,2-dimethyl-propyl)-amide

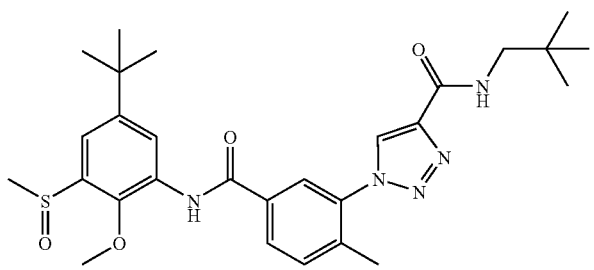

1-[5-(5-tert-Butyl-3-medthanesulfinyl-2-methoxy-phenylcarbamoyl)-2-methyl-phenyl]-1H-[1,2,3]triazole-4-carboxylic acid (2,2-dimethyl-propyl)-amide

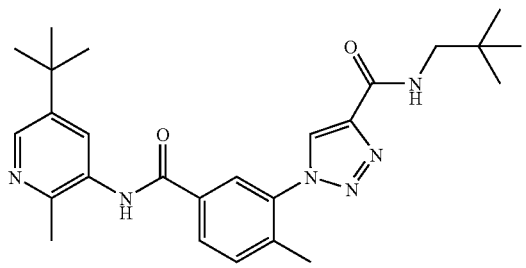

1-[5-(5-tert-Butyl-2-methyl-pyridin-3-ylcarbamoyl)-2-methyl-phenyl]-1H-[1,2,3]triazole-4-carboxylic acid (2,2-dimethyl-propyl)-amide

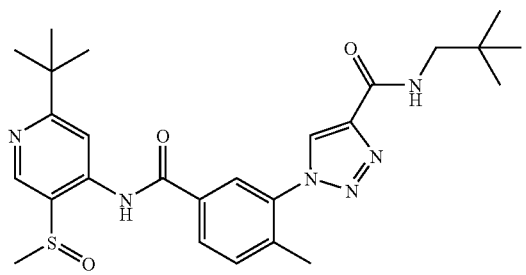

1-[5-(2-tert-Butyl-5-methanesulfinyl-pyridin-4-ylcarbamoyl)-2-methyl-phenyl]-1H-[1,2,3]triazole-4-carboxylic acid (2,2-dimethyl-propyl)-amide

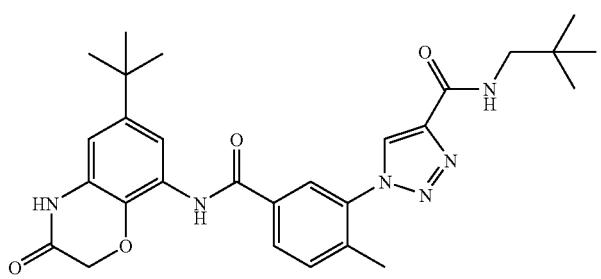

1-[5-(6-tert-Butyl-3-oxo-3,4-dihydro-2H-benzo[1,4]oxazin-8-ylcarbamoyl)-2-methyl-phenyl]-1H-[1,2,3]triazole-4-carboxylic acid (2,2-dimethyl-propyl)-amide TABLE II-continued

| | |
|---|---|
| 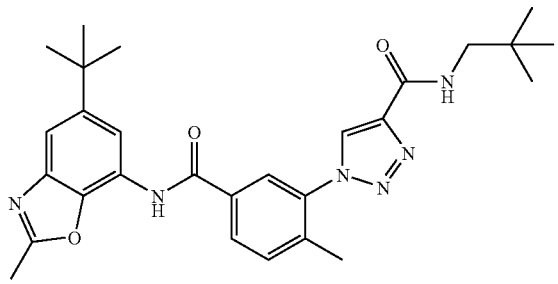 | 1-[5-(5-tert-Butyl-2-methyl-benzooxazol-7-ylcarbamoyl)-2-methyl-phenyl]-1H-[1,2,3]triazole-4-carboxylic acid (2,2-dimethyl-propyl)-amide |
| 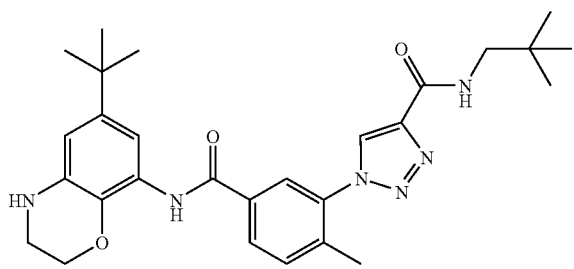 | 1-[5-(6-tert-Butyl-3,4-dihydro-2H-benzo[1,4]oxazin-8-ylcarbamoyl)-2-methyl-phenyl]-1H-[1,2,3]triazole-4-carboxylic acid (2,2-dimethyl-propyl)-amide |
| 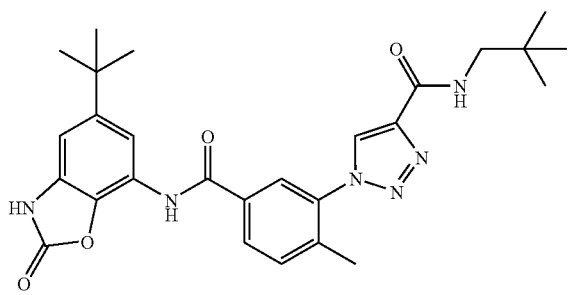 | 1-[5-(5-tert-Butyl-2-oxo-2,3-dihydro-benzooxazol-7-ylcarbamoyl)-2-methyl-phenyl]-1H-[1,2,3]triazole-4-carboxylic acid (2,2-dimethyl-propyl)-amide |
| 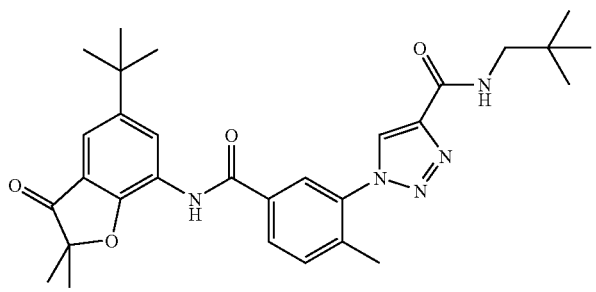 | 1-[5-(5-tert-Butyl-2,2-dimethyl-3-oxo-2,3-dihydro-benzofuran-7-ylcarbamoyl)-2-methyl-phenyl]-1H-[1,2,3]triazole-4-carboxylic acid (2,2-dimethyl-propyl)-amide |
| 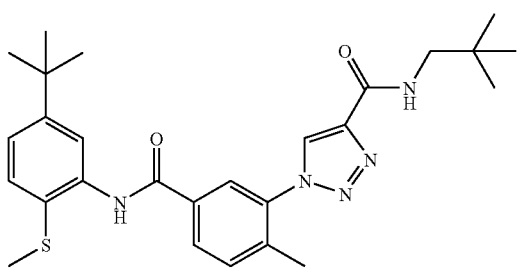 | 1-[5-(5-tert-Butyl-2-methylsulfanyl-phenylcarbamoyl)-2-methyl-phenyl]-1H-[1,2,3]triazole-4-carboxylic acid (2,2-dimethyl-propyl)-amide |

TABLE II-continued

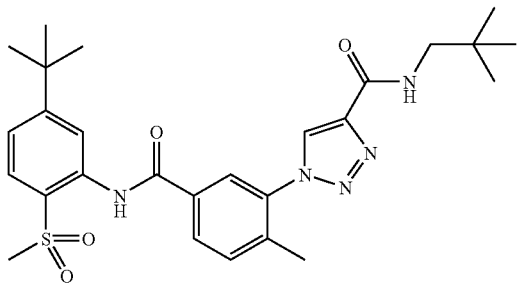

1-[5-(5-tert-Butyl-2-methanesulfonyl-phenylcarbamoyl)-2-methyl-phenyl]-1H-[1,2,3]triazole-4-carboxylic acid (2,2-dimethyl-propyl)-amide

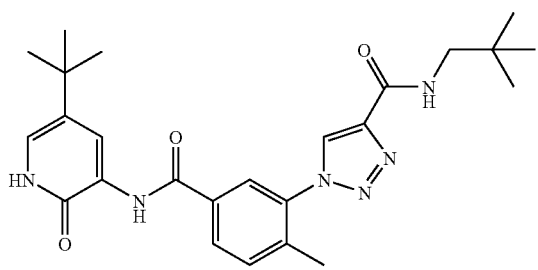

1-[5-(5-tert-Butyl-2-oxo-1,2-dihydro-pyridin-3-ylcarbamoyl)-2-methyl-phenyl]-1H-[1,2,3]triazole-4-carboxylic acid (2,2-dimethyl-propyl)-amide

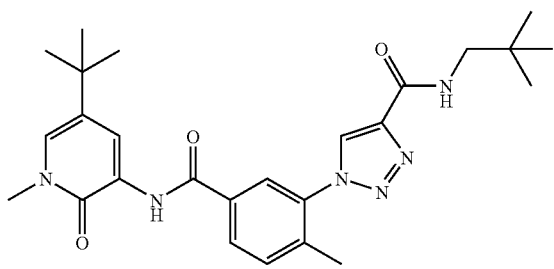

1-[5-(5-tert-Butyl-1-methyl-2-oxo-1,2-dihydro-pyridin-3-ylcarbamoyl)-2-methyl-phenyl]-1H-[1,2,3]triazole-4-carboxylic acid (2,2-dimethyl-propyl)-amide

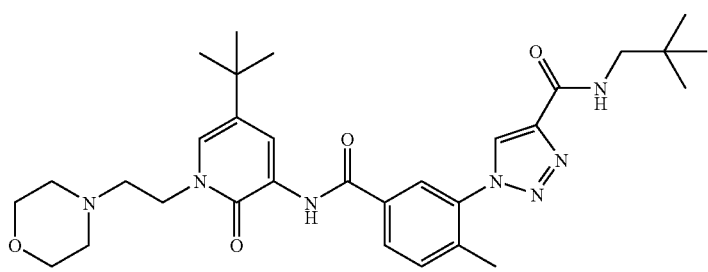

1-[{5-[5-tert-Butyl-1-(2-morpholin-4-yl-ethyl)-2-oxo-1,2-dihydro-pyridin-3-ylcarbamoyl]-2-methyl-phenyl}-1H-[1,2,3]triazole-4-carboxylic acid (2,2-dimethyl-propyl)-amide

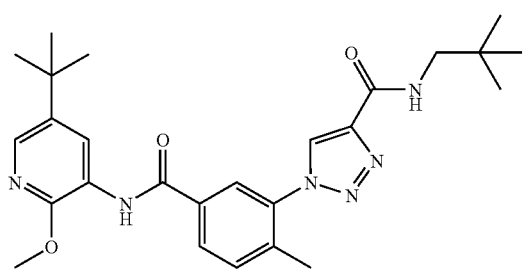

1-[5-(5-tert-Butyl-2-methoxy-pyridin-3-ylcarbamoyl)-2-methyl-phenyl]-1H-[1,2,3]triazole-4-carboxylic acid (2,2-dimethyl-propyl)-amide TABLE II-continued

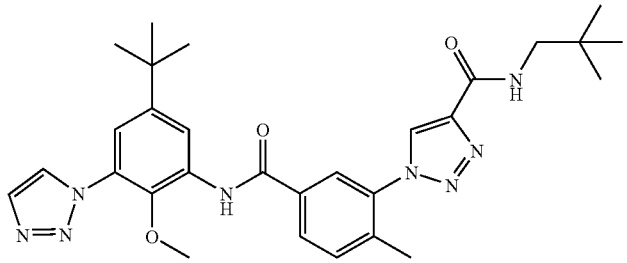

1-[5-(5-tert-Butyl-2-methoxy-3-[1,2,3]triazol-1-yl-phenylcarbamoyl)-2-methyl-phenyl]-1H-[1,2,3]triazole-4-carboxylic acid (2,2-dimethyl-propyl)-amide

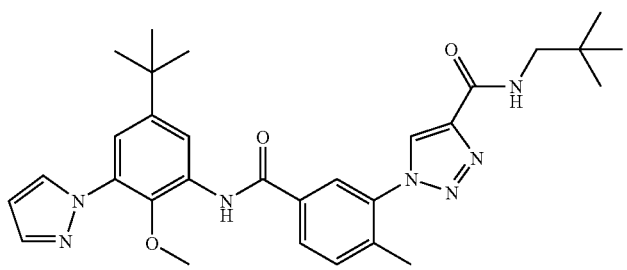

1-[5-(5-tert-Butyl-2-methoxy-3-pyrazol-1-yl-phenylcarbamoyl)-2-methyl-phenyl]-1H-[1,2,3]triazole-4-carboxylic acid (2,2-dimethyl-propyl)-amide

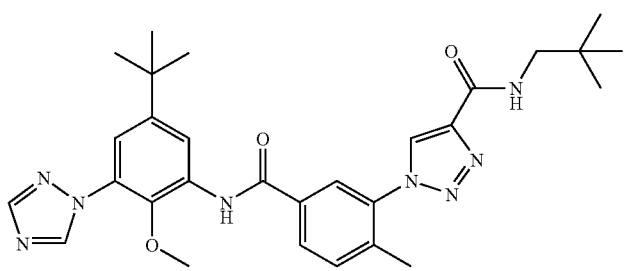

1-[5-(5-tert-Butyl-2-methoxy-3-[1,2,4]triazol-1-yl-phenylcarbamoyl)-2-methyl-phenyl]-1H-[1,2,3]triazole-4-carboxylicc acid (2,2-dimethyl-propyl)-amide

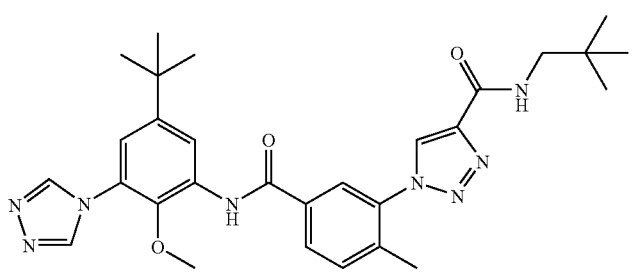

1-[5-(5-tert-Butyl-2-methoxy-3-[1,2,4]triazol-4-yl-phenylcarbamoyl)-2-methyl-phenyl]-1H-[1,2,3]triazole-4-carboxylic acid (2,2-dimethyl-propyl)-amide

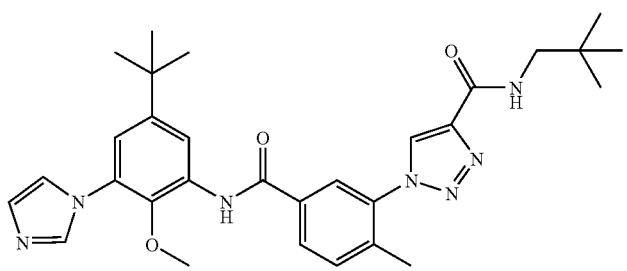

1-[5-(5-tert-Butyl-3-imidazol-1-yl-2-methoxy-phenylcarbamoyl)-2-methyl-phenyl]-1H-[1,2,3]triazole-4-carboxylic acid (2,2-dimethyl-propyl)-amide

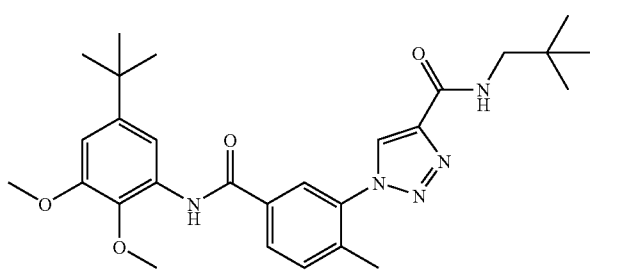

1-[5-(5-tert-Butyl-2,3-dimethoxy-phenylcarbamoyl)-2-methyl-phenyl]-1H-[1,2,3]triazole-4-carboxylic acid (2,2-dimethyl-propyl)-amide TABLE II-continued

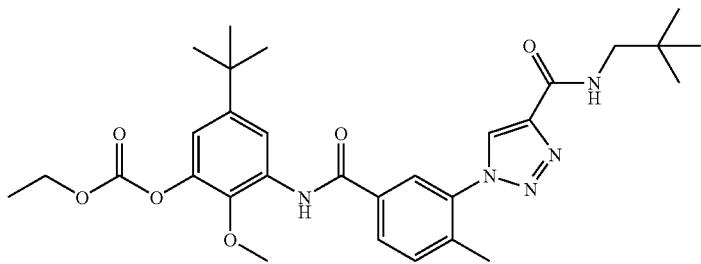

Carbonic acid 5-tert-butyl-3-{3-[4-(2,2-dimethyl-propylcarbamoyl)-[1,2,3]triazol-1-yl]-4-methyl-benzoylamino}-2-methoxy-phenyl ester ethyl ester

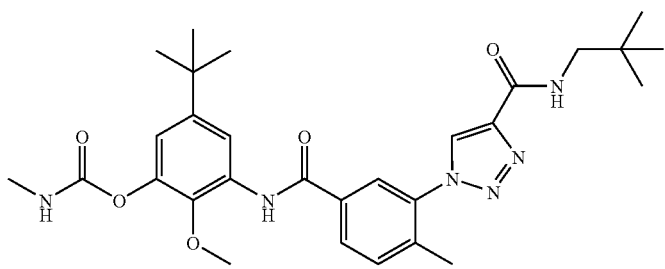

Methyl-carbamic acid 5-tert-Butyl-3-{3-[4-(2,2-dimethyl-propylcarbamoyl)-[1,2,3]triazol-1-yl]-4-methyl-benzoylamino}-2-methoxy-phenyl ester

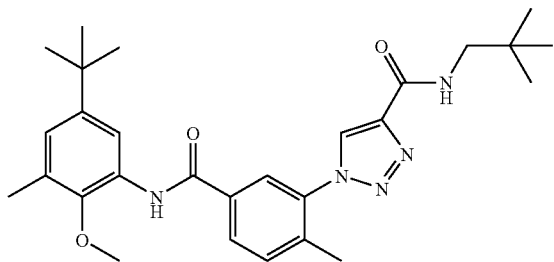

1-[5-(5-tert-Butyl-2-methoxy-3-methyl-phenylcarbamoyl)-2-methyl-phenyl]-1H-[1,2,3]triazole-4-carboxylic acid (2,2-dimethyl-propyl)-amide

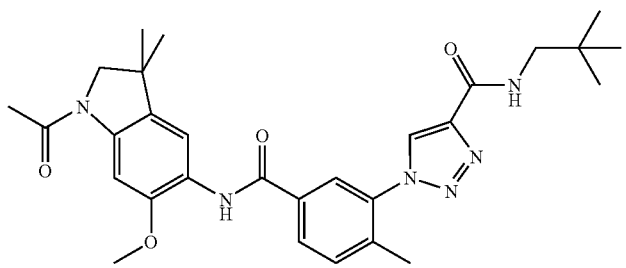

1-[5-(1-Acetyl-6-methoxy-3,3-dimethyl-2,3-dihydro-1H-indol-5-ylcarbamoyl)-2-methyl-phenyl]-1H-[1,2,3]triazole-4-carboxylic acid (2,2-dimethyl-propyl)-amide

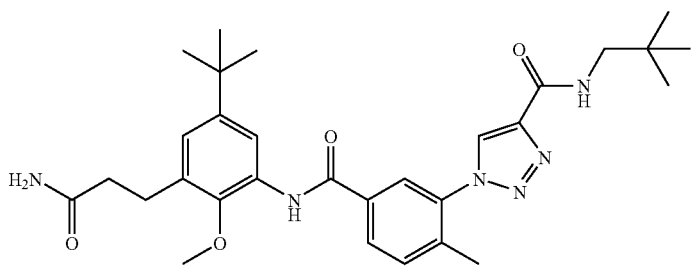

1-{5-[5-tert-Butyl-3-(2-carbamoyl-ethyl)-2-methoxy-phenylcarbamoyl]-2-methyl-phenyl}-1H-[1,2,3]triazole-4-carboxylic acid (2,2-dimethyl-propyl)-amide TABLE II-continued

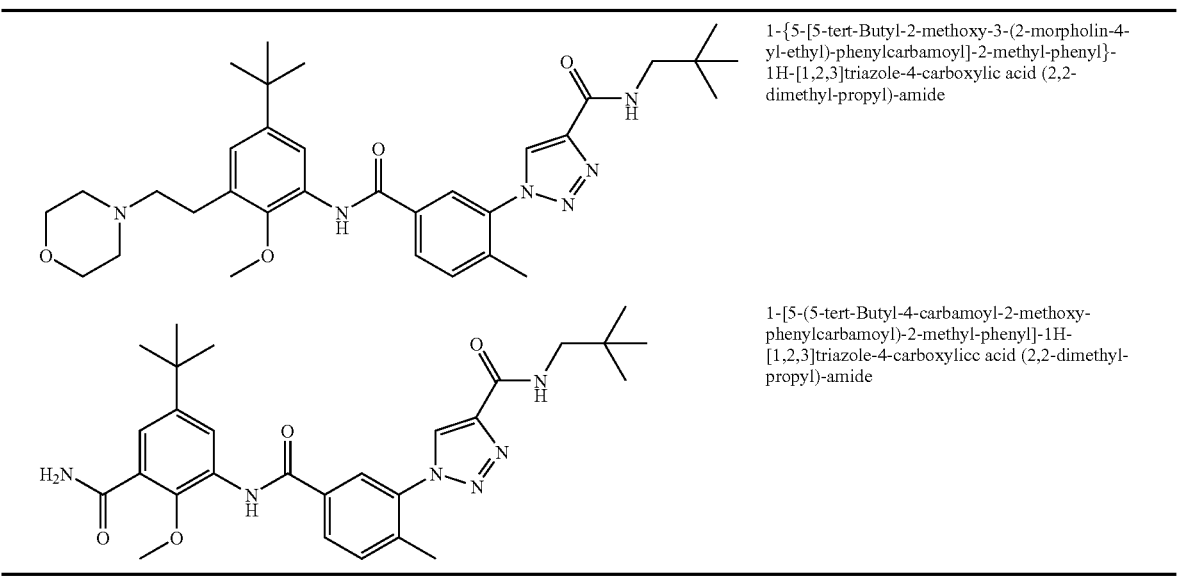

1-{5-[5-tert-Butyl-2-methoxy-3-(2-morpholin-4-yl-ethyl)-phenylcarbamoyl]-2-methyl-phenyl}-1H-[1,2,3]triazole-4-carboxylic acid (2,2-dimethyl-propyl)-amide 1-[5-(5-tert-Butyl-4-carbamoyl-2-methoxy-phenylcarbamoyl)-2-methyl-phenyl]-1H-[1,2,3]triazole-4-carboxylice acid (2,2-dimethyl-propyl)-amide or the pharmaceutically acceptable salts, acids, esters or isomers thereof.

In all the compounds disclosed hereinabove in this application, in the event the nomenclature is in conflict with the structure, it shall be understood that the compound is defined by the structure.

Of particular importance according to the invention are compounds of formula (I) for use as pharmaceutical compositions with an anti-cytokine activity.

The invention also relates to the use of a compound of formula (I) for preparing a pharmaceutical composition for the treatment and/or prevention of a cytokine mediated disease or condition.

The invention also relates to pharmaceutical preparations, containing as active substance one or more compounds of formula (I) or the pharmaceutically acceptable derivatives thereof, optionally combined with conventional excipients and/or carriers.

'Isomer' shall be understood to include any of the compounds as described above containing one or more asymmetric carbon atoms and may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

The invention includes the use of any compounds of described above containing one or more isotopically-labelled form. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N, O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The invention additionally provides for methods of making the compounds of formula (I). The compounds of the invention may be prepared by the general methods and examples presented below, and methods known to those of ordinary skill in the art. In the schemes below, unless otherwise specified, $Ar_1$, $R_1$-$R_6$ and X in the formulas shown below shall have the meanings defined for these groups in the definition of the formula (I) of the invention, described hereinabove. Intermediates used in the syntheses below are either commercially available or easily prepared by methods known to those skilled in the art. Further reference in this regard may be made to U.S. Pat. Nos. 6,358,945, 6,492,393, 6,608,052, 6,765,009 and 6,743,788, US publication no. U.S. 2003-0008868 A1. Each of the aforementioned are incorporated in their entirety.

Reaction progress may be monitored by conventional methods such as thin layer chromatography (TLC). Intermediates and products may be purified by methods known in the art, including column chromatography, HPLC or recrystallization.

Compounds of formula (I) having $R_5$=—$OR^a$ may be prepared as described in Scheme I.

Scheme I

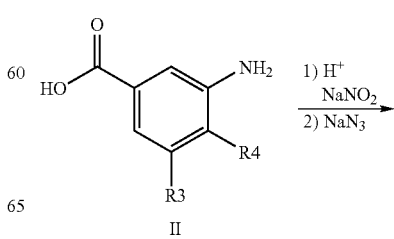

II

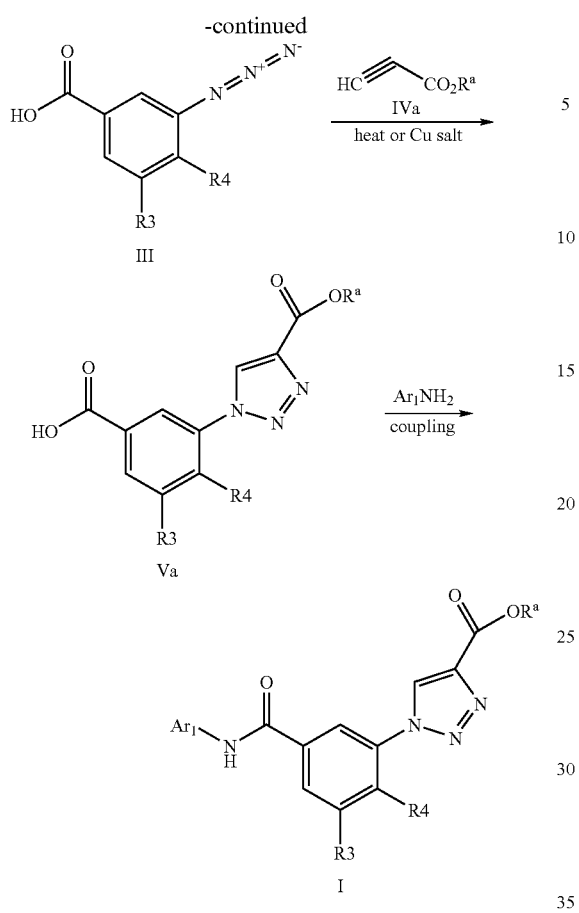

Compounds of formula (I) in which $R_5$ is an aryl, cycloalkyl, heteroaryl or heterocyclyl group may be prepared from III as illustrated in Scheme II.

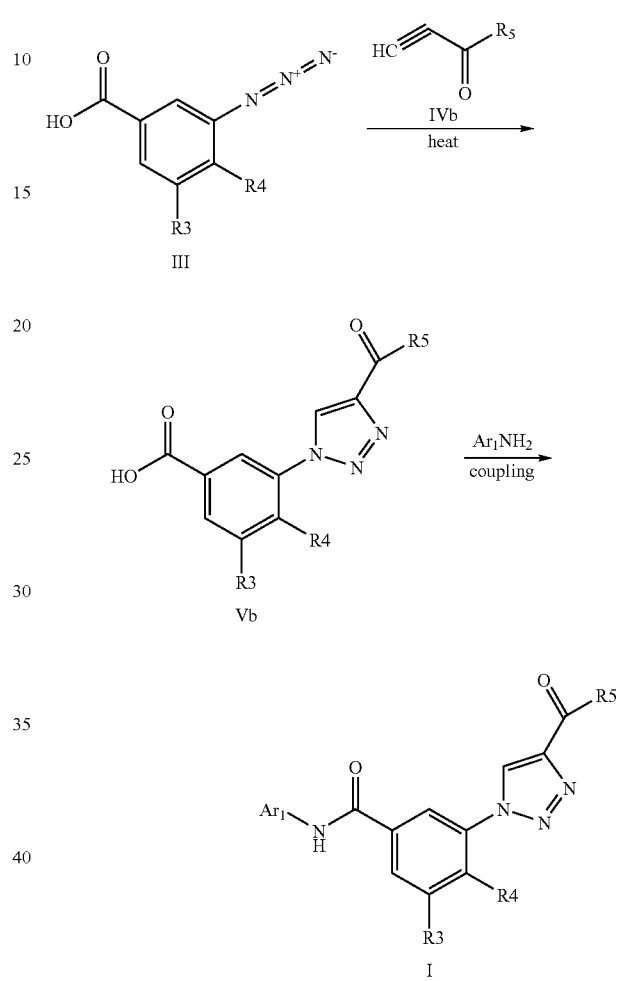

As illustrated in Scheme I, an optionally substituted 3-aminobenzoic acid (II) is reacted with $NaNO_2$ in an acidic solution such as 2N HCl or trifluoroacetic acid, at about 0° C. The diazonium salt that forms is reacted in situ with a cold aqueous solution of $NaN_3$ at about 0° C. to provide the azide III. Reaction of the azide with alkyne ester IVa, either by heating at about 80° C. to 100° C. in a sealed tube in a suitable solvent such as dimethylacetamide (DMA) or toluene, or treating with a copper salt, such as CuI in acetonitrile or $Cu_2SO_4$ with sodium ascorbate in ethanol and water, provides the triazole V and its regioisomer. Intermediate V is then coupled with the desired aniline $Ar_1NH_2$ by methods known in the art to produce the desired compound of formula (I) having $R_5=OR^a$. Coupling methods may include conversion of the benzoic acid V to the acid chloride, for example by treatment with oxalyl chloride and DMF in a suitable solvent such as dichloromethane or THF, followed by reaction with the desired aniline compound $Ar_1NH_2$ in the presence of a suitable base such as 2,6-lutidine or a tertiary amine, in a suitable solvent such as dichloromethane. Alternatively, one may react the benzoic acid V with $Ar_1NH_2$ under standard peptide coupling conditions known in the art, for example, treatment of V with 1-(3-dimethylaminopropyl)-3-ethylcarbodiimide (EDC) and 1-hydroxybenzotriazole (HOBt) in a suitable solvent such as DMF, followed by addition of $Ar_1NH_2$. The initially formed (I) may be further modified by methods known in the art to provide additional compounds of the invention. Some of these methods are illustrated in the Synthetic Examples section below.

Reaction of III with an alkyne substituted with the desired $R_5$ (IVb) as described above for the alkyne ester (IVa) provides the desired ketone Vb. Coupling with $Ar_1NH_2$ as described above provides the desired compound of formula (I).

A modification of the procedure in Scheme I is illustrated in Scheme III and described below.

Scheme III

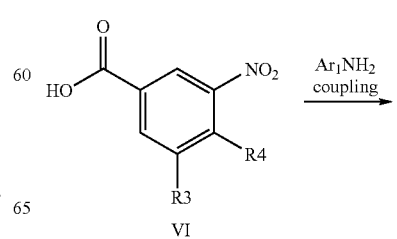

-continued

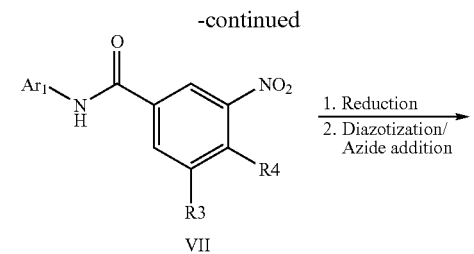

VII

1. Reduction
2. Diazotization/Azide addition

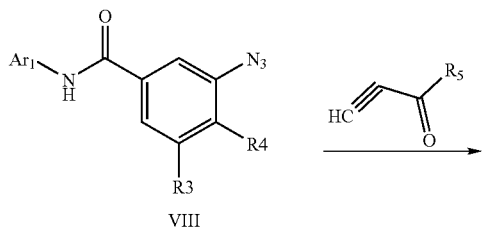

VIII

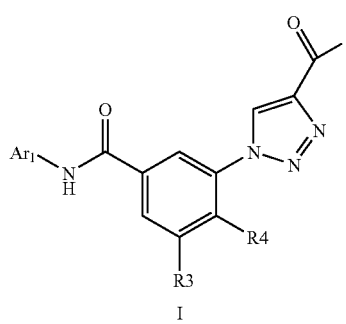

I

In this modification, one couples the 3-nitrobenzoic acid VI with the desired Ar₁NH₂ as described for the coupling steps above to form amide VII. The nitro group is then reduced by methods known in the art, for example by stirring under a hydrogen atmosphere in a suitable solvent such as MeOH with 1% HOAc, in the presence of a suitable catalyst such as palladium on carbon to provide aniline VIII. Formation of the azide followed by reaction with the desired alkyne intermediate as described above provides the desired compound of formula (I).

Compounds of formula (I) having $R_5$=—NHR$^a$ may be prepared from compounds of formula (I) having $R_5$=—OR$^a$ by methods known in the art and illustrated in Scheme IV.

Scheme IV

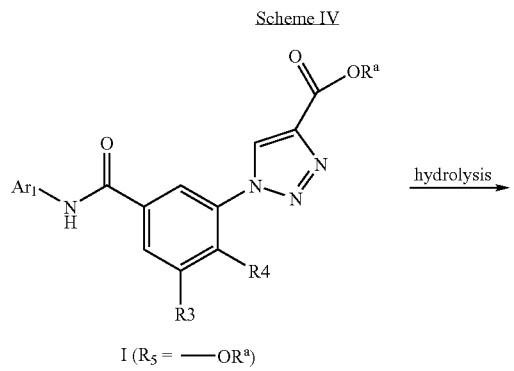

I ($R_5$ = —OR$^a$)

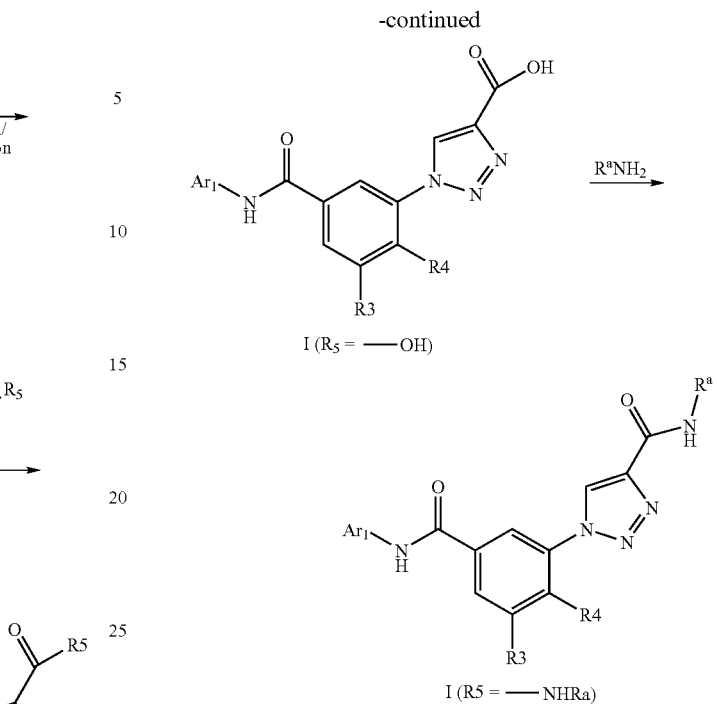

Hydrolysis of I (R=OR$^a$) for example by treatment with aqueous base in a suitable solvent such as MeOH provides carboxylic acid I ($R^5$=—OH). The carboxylic acid is then coupled with the desired amine R$^a$NH₂ by methods known in the art and described above and in the Synthetic Examples section below to provide the desired compound.

Aniline compounds Ar₁NH₂ are readily prepared from commercially available intermediates by methods known in the art. Further reference in this regard may be made to references cited in the first paragraph of this section.

SYNTHETIC EXAMPLES

Intermediate 1; Intermediate 2

A mixture of 1.11 g (6.27 mmol) of 3-azido-4-methyl benzoic acid and 12.5 mmol of alkyl propiolate (HCC—CO₂R), was stirred in 4.2 mL of DMA at 110° C. in a sealed tube overnight. The resulting brown solution was poured into water, and the resulting precipitate was filtered, and then recrystallized from EtOH/water to provide alkyl 1-(2-methyl-5-carboxyphenyl)-[1,2,3]triazole-4-carboxylate. Recrystallization from EtOH provided isomerically pure triazole.

| Intermediate | Alkyl propiolate | R | Name |
|---|---|---|---|
| 1 | ethyl propiolate | Et | ethyl 1-(2-methyl-5-carboxyphenyl)-[1,2,3]triazole-4-carboxylate |
| 2 | methyl propiolate | Me | methyl 1-(2-methyl-5-carboxyphenyl)-[1,2,3]triazole-4-carboxylate |

Intermediate 3; Intermediate 4

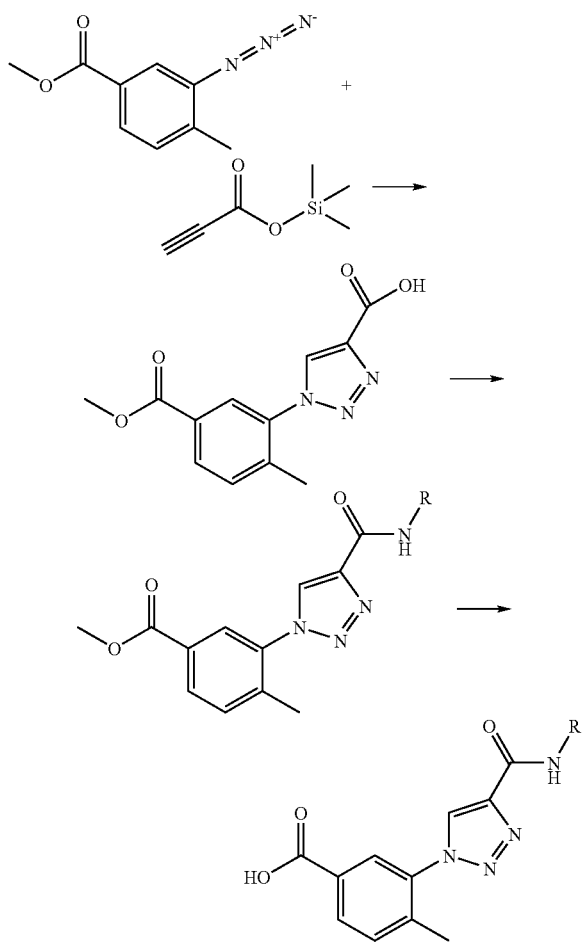

3-Azido-4-methyl-benzoic acid methyl ester (878 mg, 4.60 mmol) and trimethylsilyl propiolate (777 mg, 5.05 mmol) were heated to 80° C. in a sealed tube overnight. The tube was cooled and the contents were mixed with 20 mL of MeOH. After 2 h, the mixture was poured into rapidly stirring cold water, and the resulting precipitate was filtered and dried under air to provide 823 mg of 1-(5-Methoxycarbonyl-2-methyl-phenyl)-1H-[1,2,3]triazole-4-carboxylic acid.

The above triazole carboxylic acid (780 mg, 2.99 mmol) was dissolved in 6 mL of DMF and stirred at rt while 1.8 g (4.73 mmol) of HATU was added. Once the HATU dissolved, 1.69 mL of iPr$_2$NEt was added slowly, and the reaction vessel was placed in a 0° C. bath. An amine (4.73 mmol) was then added slowly, and the vessel was warmed slowly to rt. After 30 min, the mixture was poured into ice-cold water. When a precipitate formed, it was filtered and washed with water. Otherwise, the mixture was then extracted twice with EtOAc, and the extracts washed with water and brine. The combined organic extracts were dried with Na$_2$SO$_4$, filtered and concentrated. When necessary, the resulting red residue was chromatographed to provide the pure amide. The amide was dissolved in 12 mL of MeOH and 2.23 mL of 4M NaOH was slowly added. After stirring for 2 h, half the solvent was removed and 100 mL of water was added. The pH was adjusted to <2 by the addition of conc. HCl. The resulting precipitate was filtered and dried, first under a flow of air, and second in vacuo to provide Intermediate 3 or 4.

| Intermediate | Amine (RNH$_2$) | Name |
|---|---|---|
| 3 | neopentylamine | 3-[4-(2,2-Dimethyl-propylcarbamoyl)-[1,2,3]triazol-1-yl]-4-methyl-benzoic acid |
| 4 | 1-phenylethylamine | 4-Methyl-3-[4-(1-phenylethylcarbamoyl)-[1,2,3]triazol-1-yl]-benzoic acid |

Intermediate 5

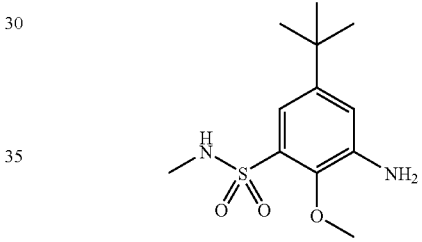

3-Amino-5-tert-butyl-2-methoxy-N-methyl-benzene-sulfonamide. To a solution of 5-tert-Butyl-2-methoxy-3-nitro-phenylamine (900 mg, 4.01 mmol) in 5 mL of HOAc was carefully added 5 mL of conc. HCl. The solution cooled in ice/salt bath with. A solution of 500 mg of NaNO$_2$ in 2 mL of water was added dropwise at 0° C. The resulting black slurry was stirred for 30 min at 0° C. A beaker was charged with 20 mL of HOAc and 400 mg of CuCl. Gaseous SO$_2$ carefully bubbled throught the mixture for 20 min, until most of the solids have dissolved and the color changes from green-yellow to blue-green. This solution was cooled to 0° C. and the diazonium salt suspension was added portionwise to SO$_2$ solution. Nitrogen gas was vigorously evolved. Ice (200 g) was then added and the resulting mixture was transferred to a seperatory funnel. The mixture was extracted with 100 mL of Et$_2$O, and the extract was washed with sat'd until all acid was neutralized (~7×30 mL). The organic layer was dried over MgSO$_4$, filtered, and concentrated. The residue was dissolved in 25 mL of 2 M CH$_3$NH$_2$ in MeOH, stirred for 30 min, and concentrated. The resulting residue was dissolved in Et$_2$O (60 mL) and washed with 1M HCl (3×20 mL), water (20 mL), and brine (20 mL). The extract was dried over MgSO$_4$, filtered, and concentrated. Recrystallization from hexanes/EtOAc provided 380 mg of a pale-brown powder. M+found 303 (M+H).

Intermediate 6

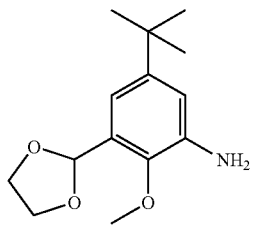

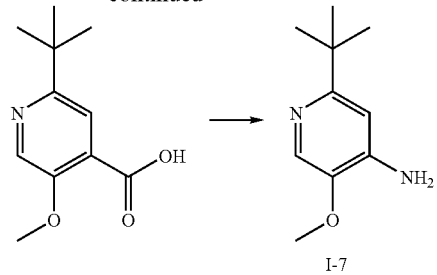

5-tert-Butyl-3-[1,3]dioxolan-2-yl-2-methoxy-phenylamine: To a solution of 15.0 g (84.2 mmol) of 5-tert-Butyl-2-hydroxy-benzaldehyde in MeCN at −30° C. was added 14.5 g (109.4 mmol) of nitronium tetrafluoborate. The temperature was allowed to climb slowly to −12° C. ove 1 h. The mixture was partitioned between sat'd NaHCO$_3$ and EtOAc. The organic layer was washed with water and brine then dried over MgSO$_4$. After filtration and evaporation, 5-tert-butyl-2-hydroxy-3-nitro-benzaldehyde was obtained as yellow solid. To a portion of this material (6.27 g, 28.1 mmol) in 40 mL of DMF was added 19.4 g of K$_2$CO$_3$ in two batches. To this slurry was added 6.12 mL (98.3 mmol) of MeI. The mixture was stirred overnight, filtered, and diluted with EtOAc. This mixture was washed with water, and the wash was then extracted with EtOAc (3×150 mL). The extracts were washed with water and brine, then dried over MgSO$_4$, filtered, and concentrated. Chromatography (5% EtOAc in hexanes) provided 5.38 g of 5-tert-butyl-2-methoxy-3-nitro-benzaldehyde as an off-white solid.

A solution of 1.0 g (4.2 mmol) of 5-tert-Butyl-2-methoxy-3-nitro-benzaldehyde, 1.18 mL of ethylene glycol, and 0.4 g of pTSA hydrate in 50 mL of benzene was refluxed for 24 h under Dean-Stark conditions. The benzene was evaporated and the resultant oil was redissolved in EtOAc. The organic layer was washed with water, sat'd NaHCO$_3$, and brine. The extract was dried over MgSO$_4$, filtered, and concentrated. Chromatography (10% EtOAc in hexanes) provided 1.0 g of 2-(5-tert-Butyl-2-methoxy-3-nitro-phenyl)-[1,3]dioxolane as a light yellow oil.

To a solution of 841 mg (2.99 mmol) of 2-(5-tert-Butyl-2-methoxy-3-nitro-phenyl)-[1,3]dioxolane in 30 mL of THF was added 252 mg of Pd/C. The reaction chamber was evacuated under vacuum and charged with hydrogen from a balloon. The solution was stirred at rt overnight. The solution was filtered through a plug of celite with EtOAc and the solvent was evaporated to give a colourless solid. Chromatography (35% EtOAc/hex) provided Intermediate 6 as a colorless solid.

Intermediate 7

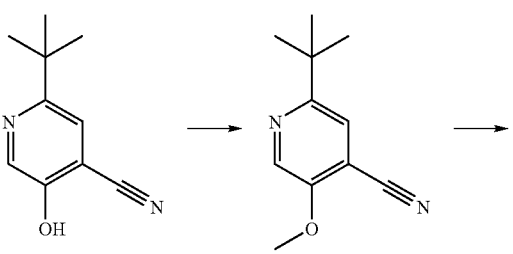

2-tert-Butyl-5-methoxy-pyridin-4-ylamine: To a solution of 10.0 g (73.5 mmol) of 2-tert-Butyl-5-hydroxy-isonicotinonitrile ((a) J. Med. Chem. 1981, 24, 115 (b) U.S. Pat. No. 4,123,537) in MeCN/MeOH (9:1, 20 mL) was added iPr$_2$NEt (1.48 mL, 8.52 mmol) followed by (trimethylsilyl)diazomethane (2.0 M in hexane, 4.30 mL, 8.52 mmol). The red solution was stirred 18 h at rt then concentrated. The residue was dissolved in CH$_2$Cl$_2$, washed with saturated NaHCO$_3$, dried over Na$_2$SO$_4$, filtered, and concentrated to provide 2-tert-Butyl-5-methoxy-isonicotinonitrile (1.10 g, 99%) as a pale yellow oil which was utilized without further purification.

The above nitrile (1.10 g, 5.68 mmol) was dissolved in H$_2$SO$_4$ (9.0 M, 6.0 mL) and heated to 120° C. for 8 h. The solution was cooled to rt and NaOH (~2.0 g) was added slowly to neutralize the solution. The mixture was then diluted with an equal volume of saturate KH$_2$PO$_4$ and extracted several times with 25% 2-propanol in chloroform. The extracts were combined, dried over Na$_2$SO$_4$, filtered, and concentrated to provide 2-tert-butyl-5-methoxy-isonicotinic acid (1.09 g, 92%) as a pale brown solid which was utilized without further purification.

Ethyl chloroformate (101 μL, 1.05 mmol) was added dropwise to a cooled solution of 2-tert-butyl-5-methoxy-isonicotinic acid (200 mg, 0.96 mmol) and iPr$_2$NEt (183 μL, 1.05 mmol) in acetone (1.0 mL) at 0° C. The mixture was stirred for 0.5 h at 0° C. then warmed to rt and stirred for an additional 0.5 h. A solution of NaN$_3$ (5.0M in water, 400 μL, 2.00 mmol) was added and the resultant slurry was stirred at rt for 1 h. Water was added to the reaction mixture and the aqueous phase was extracted with CH$_2$Cl$_2$. Toluene (2 mL) was added to the combined extracts which were subsequently dried over Na$_2$SO$_4$, filtered, and concentrated to a volume of 1 mL. The resultant toluene solution of the acyl azide was then added dropwise to a refluxing solution of benzyl alcohol (120 μL, 1.15 mmol) in toluene (1 mL) and the mixture was heated at reflux for an additional 1.5 h. Concentration, followed by filtration of the residue through a plug of silica-gel with diethyl ether provided a residue that was immediately dissolved in ethanol/water (10:1, 3.0 mL) in a Parr hydrogenation vessel and Pd(OH)$_2$ (20% on carbon, 20 mg) was added. The reaction was placed under a hydrogen atmosphere (50 psi) and shaken at rt for 0.25 h. The solution was then filtered through celite, concentrated and the residue was purified by silica-gel chromatography (EtOAc) to provide Intermediate 7 (95 mg, 56%) as a white solid.

Intermediate 8

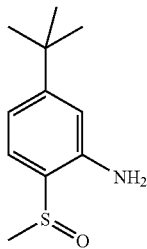

5-tert-Butyl-2-methanesulfinyl-phenylamine: Triflic anhydride (4.14 mL, 24.6 mmol) was added dropwise to a solution of 2-nitro-4-tert-butyl phenol (4.00 g, 20.5 mmol) and pyridine (2.16 mL, 26.7 mmol) in $CH_2Cl_2$ (50 mL) at 0° C. The yellow solution was stirred 0.25 h at 0° C., poured onto saturated $NaHCO_3$ and extracted with $CH_2Cl_2$. The combined extracts were washed with saturated $NaHCO_3$, dried over $Na_2SO_4$, filtered, and concentrated. The residue was purified by filtration through a plug of silica-gel (methylene chloride) to provide trifluoro-methanesulfonic acid 4-tert-butyl-2-nitro-phenyl ester (5.82 g, 87%) as a pale yellow oil.

Sodium thiomethoxide (1.86 g, 26.6 mmol) was was added to a cooled solution of the above triflate (5.80 g, 17.7 mmol) in DMF (35 mL) at 0° C. The red solution was warmed to rt for 0.75 h, poured onto saturated $NaHCO_3$ and the aqueous layer was extracted with hexane. The combined extracts were washed with saturated $NaHCO_3$, dried over $Na_2SO_4$, filtered, and concentrated to provide a mixture (1:1) of the thioether product and 2-nitro-4-tert-butylphenol. The residue was purified by recrystallization from hexane to provide a yellow precipitate that was filtered off and washed with hexane. The remaining filtrate was concentrated and chromatographed (3% diethyl ether in hexanes). The purified products were combined to provide 4-tert-butyl-1-methylsulfanyl-2-nitro-benzene (2.19 g, 55%) as a bright yellow solid.

Sodium periodate (1.23 g, 5.76 mmol) in water (2.0 mL) was added to a solution of the above thioether (1.08 g, 4.80 mmol) in MeOH/THF (2:1, 15 mL). The mixture was stirred at 50° C. for 24 h, and then concentrated. The residue was diluted with $Et_2O$ and washed with water and saturated $NaHCO_3$, dried over $Na_2SO_4$, filtered, and concentrated. Purification by silica-gel chromatography (0-50% EtOAc in $CH_2Cl_2$) provided 4-tert-butyl-1-methanesulfinyl-2-nitro-benzene (1.05 g, 91%) as a white solid.

Tin(II)chloride dihydrate (2.84 g, 12.6 mmol) was added to a solution of the above sulfoxide (1.01 g, 4.19 mmol) in EtOAc (20 mL). The mixture was heated to reflux for 0.25 h upon which the solution became red in color. The solution was cooled to rt and poured onto 2.0 M NaOH. The aqueous phase was extracted with $Et_2O$ and the combined organic layers were washed with saturated $NaHCO_3$. The combined organic extracts were dried over $Na_2SO_4$, filtered and concentrated. The residue was dissolved in $Et_2O$ and extracted (3×) with 1.0 M HCl. The pH of the combined aqueous layers was adjusted to pH=10 with $NaHCO_3$ and extracted with $CH_2Cl_2$. The combined organic layers were dried over $Na_2SO_4$, filtered and concentrated to provide Intermediate 8 (693 mg, 78%) as a white solid.

Intermediate 9

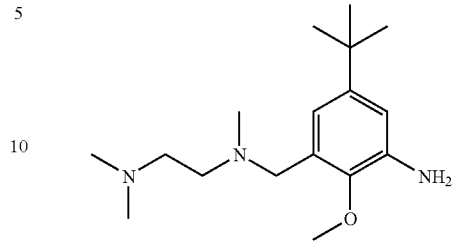

N-(3-Amino-5-tert-butyl-2-methoxy-benzyl)-N,N'N'-trimethyl-ethane-1,2-diamine: 5-tert-Butyl-2-methoxy-3-nitro-benzaldehyde (1.01 g, 4.257 mmol) was partially dissolved in 20 mL of warm MeOH, and 0.2 mL of HOAc was added. N,N,N'-trimethyl-ethane-1,2-diamine (0.61 mL, 4.7 mmol) was added and the mixture was stirred for 20 min. The reaction vessel was then placed into a 0° C. bath, and 535 mg (8.51 mmol) of $NaBH_3CN$ was added. The mixture was stirred overnight, then aq. $NaHCO_3$ was added and the mixture was concentrated to ca. half volume. The resulting mixture was then partitioned between EtOAc and sat. $NaHCO_3$. The extract was washed with brine. The washes were extracted once with EtOAc and the combined extracts were dried with $Na_2SO_4$ before being filtered and concentrated. Chromatography (1-7.5% MeOH (0.5% $NH_4OH$) in dichloromethane) provided 704 mg of N-(5-tert-Butyl-2-methoxy-3-nitro-benzyl)-N,N'N'-trimethyl-ethane-1,2-diamine as a red oil.

To 700 mg (2.16 mmol) of the abolve nitroanilsole in 10 ml of 1% HOAc was added 70 mg of Pd/C and the mixture was stirred under an $H_2$ atmosphere overnight. The mixture was filtered through celite and washed with MeOH, concentrated to a small volume, taken up in EtOAc, and washed with $NaHCO_3$. The wash was extracted twice more with EtOAc, and the combined extracts were dried with $Na_2SO_4$ before being filtered and concentrated to provide 521 mg of Intermediate 9.

Intermediate 10

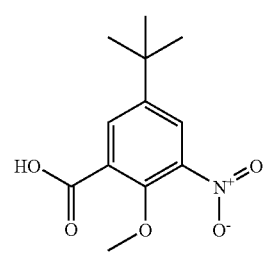

5-tert-Butyl-2-methoxy-3-nitro-benzoic acid: To a suspension of 2.10 g (10.1 mmol) of 2-methoxy-5-tert-butylbenzoic acid in 6 mL of conc $H_2SO_4$ cooled in an ice bath was added dropwise a solution of 1 mL (11.1 mmol) of $HNO_3$ in 2 ml $H_2SO_4$. The mixture was stirred, warming from 0° C. to rt over 3 h. The mixture was then poured into crushed ice and the resulting precipitate was filtered and dried. Recrystallization from 1:1 water/EtOH (8 mL/g) provided 1.4 g of product Intermediate 10.

Intermediate 11

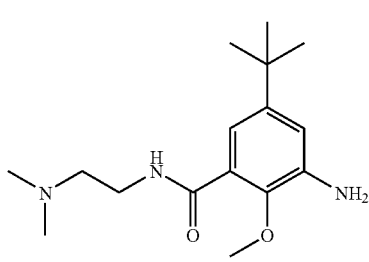

3-Amino-5-tert-butyl-N-(2-dimethylamino-ethyl)-2-methoxy-benzamide: A mixture of 2.15 g (8.49 mmol) of Intermediate 10 and 1.90 g (16.0 mmol) of SOCl$_2$ in 20 ml of CH$_2$Cl$_2$ was heated to reflux for 4 h. The mixture was concentrated, and the resulting residue was dissolved in 20 ml of CH$_2$Cl$_2$, cooled in an ice bath, and 2.23 ml (16.0 mmol) of Et$_3$N and 1.09 mL (9.35 mmol) of N,N-dimethylethylenediamine was added. The mixture was stirred overnight, then was diluted with EtOAc, washed with water and brine, dried (Na$_2$SO$_4$), filtered and concentrated to provide 2.0 g of 2-methoxyl-3-nitro-5-tert-butylbenzoic acid as a yellow oil. This material (2.90 g, 8.97 mmol) and 500 mg of Pd/C in 100 ml of EtOAc was stirred under a H$_2$ atmosphere overnight. Another 100 mg of Pd/C was added, and the mixture was stirred and additional 48 h under an H$_2$ atmosphere. The mixture was filtered through a celite, and the filtrate was concentrated to give 2.6 g of Intermediate 11.

Intermediate 12

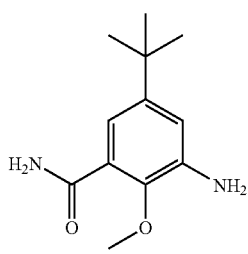

3-Amino-5-tert-butyl-2-methoxy-benzamide: A mixture of 2.00 g (7.90 mmol) of Intermediate 10 and 1.90 g (16.0 mmol) of SOCl$_2$ in 20 ml of CH$_2$Cl$_2$ was heated to reflux for 4 h. The mixture was concentrated, and the resulting residue was dissolved in 20 ml of CH$_2$Cl$_2$, cooled in an ice bath, and 2.23 ml (16.0 mmol) of Et$_3$N and 2 mL of conc. NH$_4$OH were added. The mixture was stirred for 2 h and the mixture was diluted with EtOAc, washed with water and brine, dried (Na$_2$SO$_4$), filtered and concentrated to provide 2.0 g of 2-methoxyl-3-nitro-5-tert-butylbenzoic acid as a yellow oil. This material (2.00 g, 7.93 mmol) and 400 mg of Pd/C in 100 ml of EtOAc was stirred under a H$_2$ atmosphere overnight. The mixture was filtered through a celite, and the filtrate was concentrated to give 1.75 g of Intermediate 12.

Intermediate 13

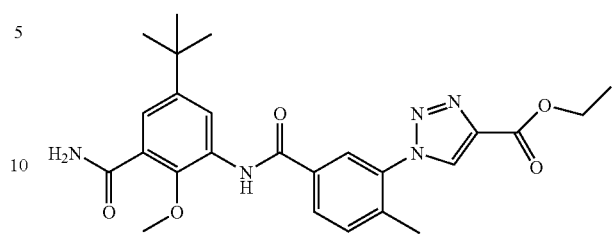

1-[5-(5-tert-Butyl-3-carbamoyl-2-methoxy-phenylcarbamoyl)-2-methyl-phenyl]-1H-[1,2,3]triazole-4-carboxylic acid ethyl ester: Intermediate 1 (339 mg, 1.23 mmol) was dissolved in a mixture of 20 mL CH$_2$Cl$_2$ and 10 mL THF then oxalyl chloride (162 µL) was added dropwise followed by 15 µL DMF, which caused vigorous bubbling. The pale yellow solution was stirred at room temp for 30 min. then the solvent was removed in vacuo. The pale beige solid was then suspended in 30 mL CH$_2$Cl$_2$, then 260 mg (1.17 mmol) of Intermediate 12 was added followed immediately by 2,6-lutidine (430 µL) and the yellow suspension was stirred at room temp overnight. The mixture was concentrated and the residue was partitioned between EtOAc (150 mL) and water (50 mL). The layers were separated, and the precipitate suspended in the aqueous layer was filtered, washed with water, and dried to provide 225 mg of Intermediate 13.

Example 1

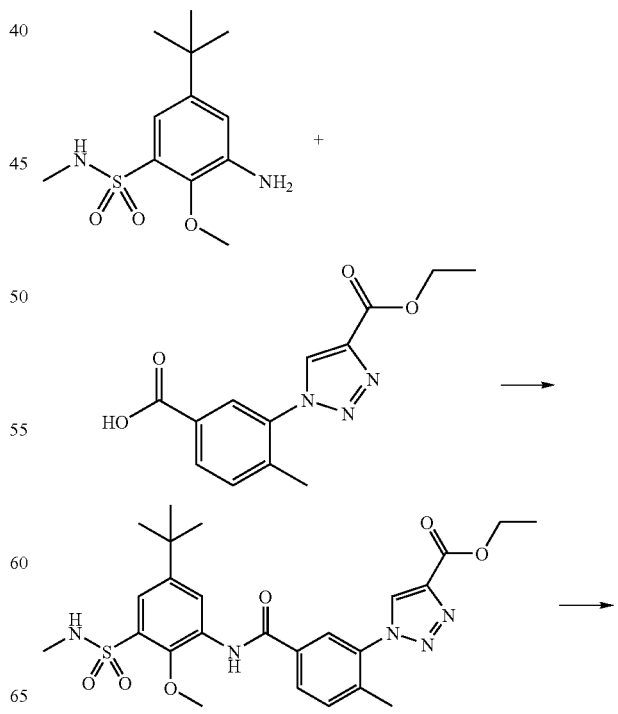

-continued

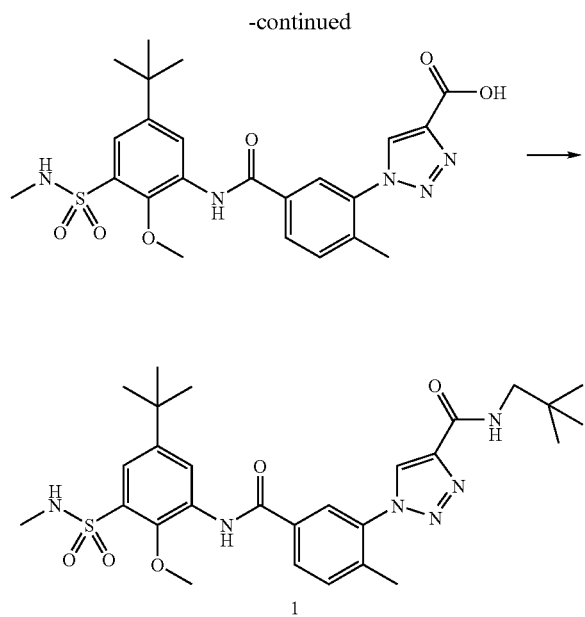

1-[5-(5-tert-Butyl-2-methoxy-3-methylsulfamoyl-phenylcarbamoyl)-2-methyl-phenyl]-1H-1,2,3-triazole-4-carboxylic acid (2,2-dimethyl-propyl)-amide: Intermediate 1 (138 mg, 0.500 mmol) was suspended in 2 mL of $CH_2Cl_2$ under nitrogen. Oxalyl chloride (0.7 mL of 2.0 M in $CH_2Cl_2$; 1.4 mmol) was added, followed by catalytic DMF. Gas was evolved as the mixture was stirred at. rt for 1 h. The solvent was removed and the resulting residue was dried under vacuum. The dry residue was dissolved in 3 mL of $CH_2Cl_2$ and a solution of 122 mg (0.448 mmol) of Intermediate 5 and 0.5 mL of triethylamine in 3 mL of $CH_2Cl_2$ was added. This solution was stirred at rt overnight. EtOAc (150 mL) was added and the mixture was washed with 2 N HCl (50 mL), sat'd $NaHCO_3$ (50 mL), and brine (100 mL). The extract was dried over $MgSO_4$, filtered, and concentrated to provide 235 mg of 1-[5-(5-tert-Butyl-2-methoxy-3-methylsulfamoylphenylcarbamoyl)-2-methyl-phenyl]-1H-[1,2,3]triazole-4-carboxylic acid ethyl ester as a light-brown foam.

The above ester (230 mg, 0.434 mmol) was dissolved in 7 mL of MeOH. A solution of 250 mg (5.99 mmol) of LiOH in 2 mL of water was added at RT. The resulting mixture was stirred overnight, then acidified with 4N HCl and extracted with EtOAc (4×30 mL). The extracts were combined, dried over $MgSO_4$, filtered and concentrated to provide 223 mg of 1-[5-(5-tert-Butyl-2-methoxy-3-methylsulfamoyl-phenylcarbamoyl)-2-methyl-phenyl]-1H-[1,2,3]triazole-4-carboxylic acid as a brown foam (>90% by LCMS).

To 220 mg (0.439 mmol) of the above acid and 100 mg of HOBt hydrate in 3 mL of DMF was added 100 mg of EDC hydrochloride. After stirring for 5 min, 102 µL (0.872 mmol) of neopentylamine was added. The mixture was stirred for 12 h and was diluted in 80 mL of EtOAc and washed with sat $NaHCO_3$ (15 mL) and brine (3×50 mL). The extract was dried over $MgSO_4$. Chromatography (0% to 50% EtOAc in hexanes) provided 122 mg of white foam of 85% purity. Recrystallization from $Et_2O$/hexanes provided 68 mg of Example 1. ESI MS m/z 594 $[C_{28}H_{38}N_6O_5S]^+$.

Example 2

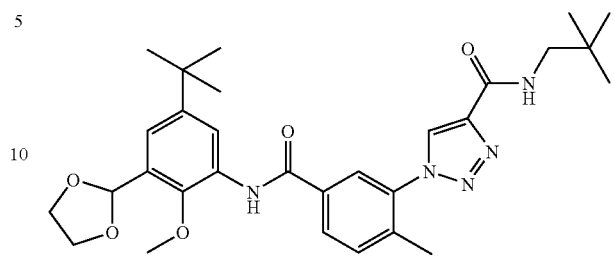

1-[5-(5-tert-Butyl-3-1,3-dioxolan-2-yl-2-methoxy-phenylcarbamoyl)-2-methyl-phenyl]-1H-1,2,3-triazole-4-carboxylic acid (2,2-dimethyl-propyl)-amide: Intermediate 3 (210 mg, 0.664 mmol) and Intermediate 6 (167 mg, 0.664 mmol), along with 379 mg of HATU, 45 mg of HOAt, and 0.35 mL of $Et_3N$ were stirred at room temperature in 2.5 mL of DMF overnight. The reaction was partitioned between EtOAc and water in a separatory funnel. The aqueous layer was extracted with EtOAc and the combined organic layers were washed with water, brine, dried over $MgSO_4$, filtered, and concentrated. The resultant oil was chromatographed (0-5% MeOH in $CH_2Cl_2$) to provide 275 mg of 2 as a yellow foam. M+: found 550 (M+H).

Example 3

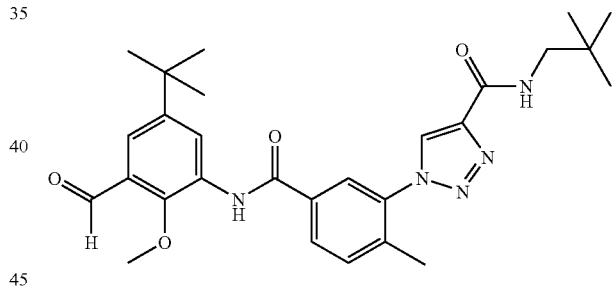

1-[5-(5-tert-Butyl-3-formyl-2-methoxy-phenylcarbamoyl)-2-methyl-phenyl]-1H-[1,2,3]triazole-4-carboxylic acid (2,2-dimethyl-propyl)-amide: To a solution of 275 mg (0.500 mmol) of Example 2 in 14 mL of MeOH was added 7 mL of 2N aq. HCl. The mixture was stirred overnight and partitioned EtOAc. The organic layer was washed with sat'd $NaHCO_3$, water, and brine, then was dried over $MgSO_4$, filtered, and was concentrated to provide 215 mg of an off-white foam.

General Procedure for the reductive amination of Example 3: To a solution of 40 mg (0.079 mmol) of Example 3 in 2.5 mL of DCE and 54 µL of AcOH cooled in an ice bath was added 1.98 mmol of the amine. The solution was allowed to come to room temperature over 30 min. At this point the 42 mg (0.40 mmol) of $(AcO)_3NaBH$ was added. The mixture was stirred overnight, and then was partitioned between EtOAc and aq. 3% $NH_4OH$. The extract was washed with water and brine, the was dried over $MgSO_4$, filtered and concentrated. Chromatography (0-5% MeOH (0.05% $NH_4OH$) in dichloromethane) provided the pure product.

| Example | Amine | Product |
|---|---|---|
| Example 4 | dimethylamine | 1-[5-(5-tert-Butyl-3-dimethylaminomethyl-2-methoxy-phenylcarbamoyl)-2-methyl-phenyl]-1H-1,2,3-triazole-4-carboxylic acid (2,2-dimethyl-propyl)-amide |
| Example 5 | 1-methyl piperazine | 1-{5-[5-tert-Butyl-2-methoxy-3-(4-methyl-piperazin-1-ylmethyl)-phenylcarbamoyl]-2-methyl-phenyl}-1H-1,2,3-triazole-4-carboxylic acid (2,2-dimethyl-propyl)-amide |
| Example 6 | dimethyl-(S)-pyrrolidin-3-yl-amine | 1-{5-[5-tert-Butyl-3-((S)-3-dimethylamino-pyrrolidin-1-ylmethyl)-2-methoxy-phenylcarbamoyl]-2-methyl-phenyl}-1H-1,2,3-triazole-4-carboxylic acid (2,2-dimethyl-propyl)-amide |
| Example 7 | morpholine | 1-[5-(5-tert-Butyl-2-methoxy-3-morpholin-4-ylmethyl-phenylcarbamoyl)-2-methyl-phenyl]-1H-1,2,3-triazole-4-carboxylic acid (2,2-dimethyl-propyl)-amide |
| Example 8 | N,N,N'-tetramethyl-ethylene diamine | 1-{5-[5-tert-Butyl-3-(2-dimethylamino-ethylcarbamoyl)-2-methoxy-phenylcarbamoyl]-2-methyl-phenyl}-1H-1,2,3-triazole-4-carboxylic acid (2,2-dimethyl-propyl)-amide |

Example 9

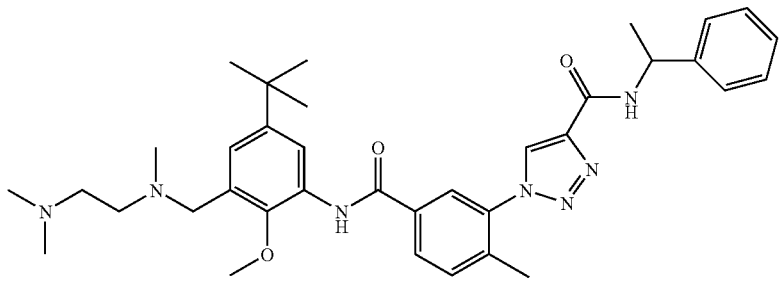

1-[5-(5-tert-Butyl-3-{[(2-dimethylamino-ethyl)-methyl-amino]-methyl}-2-methoxy-phenylcarbamoyl)-2-methyl-phenyl]-1H-[1,2,3]triazole-4-carboxylic acid (1-phenyl-ethyl)-amide: Intermediate 4 (83 mg, 0.237 mmol) and HATU were dissolved in 1 mL of DMF then chilled to 0° C. Intermediate 9 (63 mg, 0.215 mmol) was then added and mixture was stirred for 2 h. The mixture was partitioned between EtOAc and sat'd NaHCO₃, and the extract was washed with brine. The washes were extracted once more with EtOAc, and the combined extracts were dried with Na₂SO₄, filtered, and concentrated. Chromatography (0-6.5% MeOH (0.1% NH₄OH) in CH₂Cl₂) provided Example 9 as a white solid.

Example 10

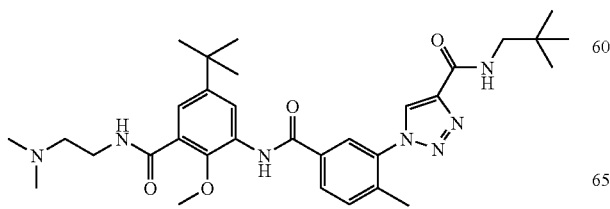

1-{5-[5-tert-Butyl-3-(2-dimethylamino-ethylcarbamoyl)-2-methoxy-phenylcarbamoyl]-2-methyl-phenyl}-1H-[1,2,3]triazole-4-carboxylic acid (2,2-dimethyl-propyl)-amide: Intermediate 11 (90 mg, 0.284 mmol) and 162 mg (0.426 mmol) of HATU were dissolved in 1 mL of DMF then chilled to 0° C. Intermediate CA (83 mg, 0.284 mmol) and 80 mL of iPr₂NEt were then added and mixture was stirred for 2 h. The mixture was partitioned between EtOAc and sat'd NaHCO₃, and the extract was washed with brine. The washes were extracted once more with EtOAc, and the combined extracts were dried with Na₂SO₄, filtered, and concentrated. Chromatography (0-6.5% MeOH (0.1% NH₄OH) in CH₂Cl₂) provided Example 10 as a white solid.

Example 12

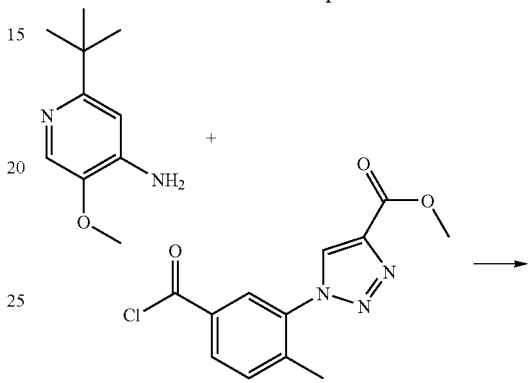

-continued

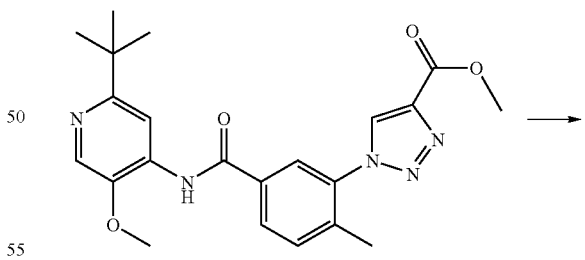

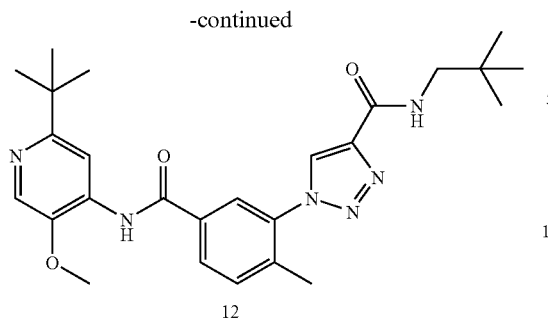

12

1-(5-Chlorocarbonyl-2-methyl-phenyl)-1H-[1,2,3]triazole-4-carboxylic acid methyl ester (90 mg, 0.322 mmol) was added to a solution of Intermediate 7 (58 mg, 0.322 mmol) and N,N-diisopropylethylamine (112 μL, 0.644 mmol) in CH$_2$Cl$_2$ (1.0 mL) at rt. The solution was stirred at rt for 2 h then poured onto saturated aqueous NaHCO$_3$. The aqueous phase was extracted with CH$_2$Cl$_2$ and the combined organic layers were washed with saturated aqueous NaHCO$_3$, dried over Na$_2$SO$_4$, filtered and concentrated. Chromatography (50% ethyl acetate in CH$_2$Cl$_2$) provided 1-[5-(2-tert-Butyl-5-methoxy-pyridin-4-ylcarbamoyl)-2-methyl-phenyl]-1H-[1,2,3]triazole-4-carboxylic acid methyl ester (105 mg, 78%) as a white solid.

LiOH (1.0M in water, 546 μL, 0.546 mmol) was added slowly to a solution of the above methyl ester (105 mg, 0.248 mmol) in THF (600 μL). Methanol (~50 μL) was added to the reaction mixture until it became homogenous. The solution was stirred at rt for 0.5 h then HCl (2.0M in diethyl ether, 273 μL, 0.546 mmol) was added and the solution was concentrated to dryness. The crude white solid 1-[5-(2-tert-Butyl-5-methoxy-pyridin-4-ylcarbamoyl)-2-methyl-phenyl]-1H-[1,2,3]triazole-4-carboxylic acid was used without further purification.

The above acid (0.248 mmol) and HATU (141 mg, 0.372 mmol) were combined in DMF (500 μL) and stirred 5 min at rt. Neopentylamine (39 μL, 0.372 mmol) was added to the reaction mixture followed by N,N-diisopropylethylamine (173 μL, 0.992 mmol). The solution was stirred at rt for 18 h and then poured onto ice cold water. The white precipitate was filtered off and washed several times with water and dried in a vacuum oven at 50° C. to provide Example 12 (120 mg, 99%) as a white solid: mp 181-182° C. (dec.); ESI MS m/z 479 [C$_{26}$H$_{34}$N$_6$O$_3$+H]$^+$.

Example 13

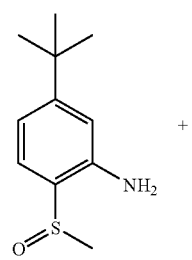

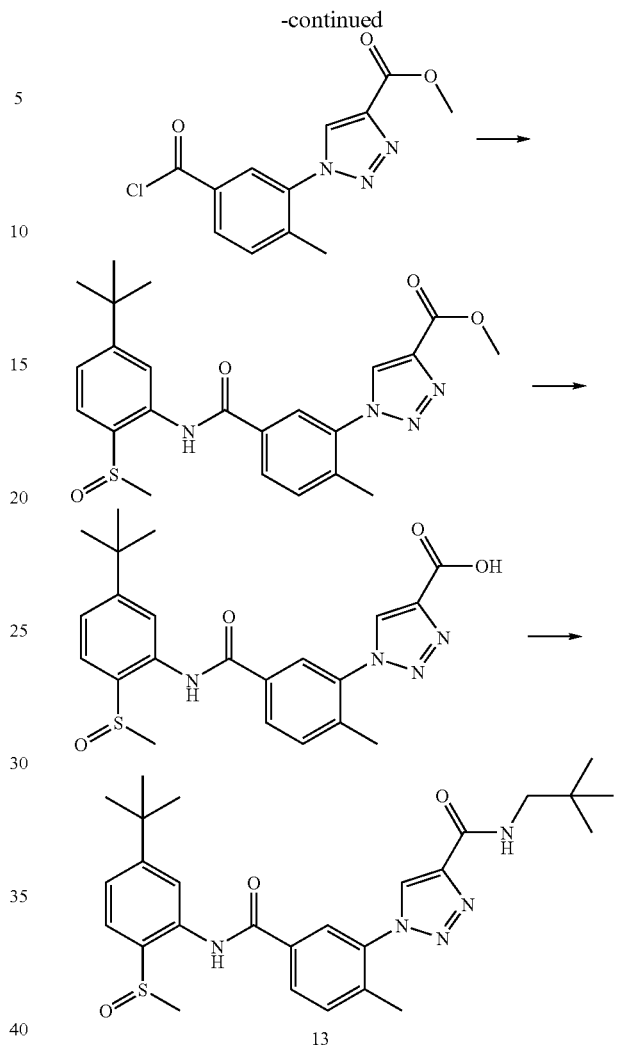

13

1-(5-Chlorocarbonyl-2-methyl-phenyl)-1H-[1,2,3]triazole-4-carboxylic acid methyl ester (137 mg, 0.492 mmol) was added to a solution of Intermediate 8 (104 mg, 0.492 mmol) and N,N-diisopropylethylamine (171 μL, 0.984 mmol) in CH$_2$Cl$_2$ (1.0 mL) at 0° C. The solution was stirred at rt for 18 h then poured onto saturated NaHCO$_3$. The aqueous phase was extracted with CH$_2$Cl$_2$ and the combined organic layers were washed with sat'd NaHCO$_3$, dried over Na$_2$SO$_4$, filtered and concentrated to provide 1-[5-(5-tert-Butyl-2-methanesulfinyl-phenylcarbamoyl)-2-methyl-phenyl]-1H-[1,2,3]triazole-4-carboxylic acid methyl ester (155 mg, 70%) as a white solid that was utilized without further purification.

LiOH (1.0 M in water, 784 μL, 0.784 mmol) was added slowly to a solution of the above ester (155 mg, 0.341 mmol) in THF (1.0 mL). Methanol (100 μL) was added to the reaction mixture until it became homogenous. The solution was stirred at rt for 1 h, concentrated, and the residue dissolved in saturated KH$_2$PO$_4$. The aqueous layer was extracted with chloroform and the combined extracts were dried over sodium sulfate, filtered, and concentrated. The crude white solid 1-[5-(5-tert-Butyl-2-methanesulfinyl-phenylcarbamoyl)-2-methyl-phenyl]-1H-[1,2,3]triazole-4-carboxylic acid (136 mg, 91%) was used immediately without further purification.

The above acid (136 mg, 0.309 mmol) and HATU (176 mg, 0.464 mmol) were combined in DMF (620 µL) and stirred for 5 min at rt. Neopentylamine (55 µL, 0.464 mmol) was added to the reaction mixture followed by N,N-diisopropylethylamine (161 µL, 0.927 mmol). The solution was stirred at rt for 18 h then poured onto ice cold water. The white precipitate was filtered off and washed several times with water. Purification by silica-gel chromatography (50% ethyl acetate in $CH_2Cl_2$) provided Example 13 (91 mg, 58%) as a white solid: mp 74-78° C. (dec.); ESI MS m/z 510 $[C_{27}H_{35}N_5O_3S+H]^+$.

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in US publication no. U.S. 2004-0033222 A1.

The compounds of the invention are also p38 Map kinase inhibitors, and therefore will be useful for treating oncological diseases and other cytokine mediated diseases and conditions related to p38 Map kinase as known in the art. Methods of assaying for p38 Map kinase activity can be perfomed by known methods. See for example Branger, J. et al, *The Journal of Immunology*, (2002), 168: 4070-4077, and the 46 references cited therein, each incorporated herein by reference in their entirety. Oncological diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. Pat. No. 6,565,880, incorporated by reference herein in its entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to US publication no. U.S. 2003-0118575 A1. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Biological Assays

Inhibition of TNF Production in THP Cells

The inhibition of cytokine production can be observed by measuring inhibition of TNFα in lipopolysaccharide stimulated THP cells (for example, see W. Prichett et al., 1995, *J Inflammation,* 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THP.I cells ($2\times10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630, from *E. coli* serotype 0111.B4; stored as 1 mg/ml stock in endotoxin screened distilled $H_2O$ at −80° C.). Blanks (unstimulated) received $H_2O$ vehicle; final incubation volume was 250 μl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds have an $IC_{50}<1$ uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.,* 10, 835).

All references cited in this application including journal and patent publications, and their respective citations within each document, are incorporated herein by reference in their entirety.

What is claimed is:

1. A compound of the formula (I)

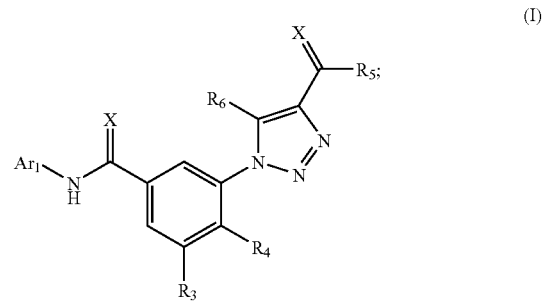

wherein:

$Ar_1$ is chosen from rings (i), (ii) or (iii) below:

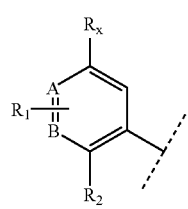

wherein one of A or B is nitrogen and the other is carbon, $R_1$ is covalently attached to either A or B, and when nitrogen is N—$R_1$ the double bond between A and B is not present;

$R_1$ is hydrogen, $NO_2$, —$N(R^{c)}{}_2$, J-C(O)—$N(R^c)$ — or J-S(O)$_m$—$N(R^{c)}$—;
  or $R^1$ is chosen from $C_{1-6}$ alkyl, $C_{3-7}$ cylcoalkyl, $C_{1-5}$ alkoxyl or $C_{3-7}$ cycloalkoxyl, $C_{1-5}$ alkylthiol or $C_{3-7}$ cycloalkylthiol, $C_{1-5}$ acyl, $C_{1-5}$ alkoxycarbonyl, $C_{1-5}$ acyloxy, $C_{1-5}$ acylamino, $C_{2-5}$ alkenyl, $C_{2-5}$ alkynyl, heterocycle, heteroaryl, or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;
  $R_2$ is chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl, oxo, $C_{1-5}$ alkylS(O)$_m$—, or amino optionally mono- or di-substituted by $C_{1-5}$ alkyl, aryl or aryl$C_{1-5}$ alkyl;

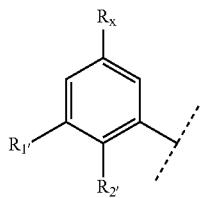
(ii)

wherein
  $R_1'$ is chosen from H, $C_{1-5}$ alkylS(O)$_m$—, $C_{1-6}$ alkyl, $C_{3-7}$ cycloalkyl, $C_{1-5}$ alkoxyl or $C_{3-7}$ cycloalkoxyl, $C_{1-5}$ alkylthiol $C_{3-7}$ cycloalkylthiol, $C_{1-5}$ acyl, $C_{1-5}$ alkoxycarbonyl, $C_{1-5}$ acyloxy, $C_{2-5}$ alkenyl, $C_{2-5}$ alkynyl, heterocycle, heterocycle$C_{1-6}$ alkyl, heteroaryl, heteroaryl$C_{1-6}$ alkyl, or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;
  $R_2'$ is chosen from nitrile, C1-5 alkylS(O)$_m$—, J-O—C(O)—O—, $NH_2$—C(O)—(CH$_2$)$_n$—, hydrogen, halogen, $C_{1-5}$ alkyl, $C_{1-5}$ alkoxy, $C_{1-5}$ alkyl$C_{1-5}$ alkoxy, hydroxyl or hydroxy $C_{1-5}$ alkyl;

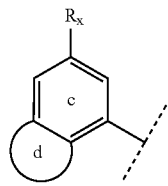
(iii)

wherein c is a benzo ring fused to ring d which is a 5-7 membered heterocyclic ring;
  each $R_x$ is chosen from $C_{1-6}$ alkyl or $C_{3-7}$ cycloalkyl each being optionally substituted by $C_{1-3}$ alkyl and optionally partially or fully halogenated, $C_{1-4}$ acyl, aroyl, $C_{1-4}$ alkoxy, which may optionally be partially or fully halogenated, halogen, $C_{1-6}$ alkoxycarbonyl, carbocyclesulfonyl and —$SO_2$—$CF_3$;
  m and n are 0,1 or 2
  and wherein $R^c$ is chosen from hydrogen or $C_{1-5}$ alkyl;
  J is chosen from $C_{1-10}$ alkyl and carbocycle each optionally substituted by $R^b$;

$R_3$, $R_4$, $R_6$, $R_7$ and $R_8$ are each independently chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl or amino optionally mono- or di-substituted by $C_{1-5}$ alkyl, aryl or aryl $C_{1-5}$ alkyl;
$R_5$ is: a bond, —O—, —S—, —N<, —NH—, C(O), a linear chain chosen from —NH(CR$_7$R$_8$)$_r$—, —(CR$_7$R$_8$)$_r$—, —O(CR$_7$R$_8$)$_r$—, —C(O)—O(CR$_7$R$_8$)$_r$—, —S(CR$_7$R$_8$)$_r$—, C(O)(CR$_7$R$_8$)$_r$—and —C(O)NH(CR$_7$R$_8$)$_r$—, wherein r is 1-5 and each of the aforementioned $R_5$ is further substituted by $R^a$,
or $R_5$ is a ring system chosen from aryl, heteroaryl or heterocyclyl each optionally substituted by $R^a$;
$R^a$ and $R^b$ are each independently chosen from hydrogen, $C_{1-5}$ alkyl, hydroxy$C_{1-5}$ alkyl, $C_{2-5}$ alkenyl, $C_{2-5}$ alkynyl, carbocycle, heterocycle, heteroaryl, $C_{1-5}$ alkoxy, $C_{1-5}$ alkylthio, amino, $C_{1-5}$ alkylamino, $C_{1-5}$ dialkylamino, $C_{1-5}$ acyl, $C_{1-5}$ alkoxycarbonyl, $C_{1-5}$ acyloxy, $C_{1-5}$ acylamino, each of the aforementioned are optionally partially or fully halogenated, or $R^a$ and $R^b$ are chosen from $C_{1-5}$ alkylsulphonylamino, hydroxy, oxo, halogen, nitro and nitrile, and
X is O or S
or a pharmaceutically acceptable salt, acid, ester or isomer thereof.

2. The compound according to claim 1 wherein
if $Ar_1$ is (i) then:
  $R_1$ is chosen from hydrogen, $C_{1-6}$ alkyl, $C_{3-7}$ cylcoalkyl, $C_{1-5}$ alkoxyl or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;
  $R_2$ is chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl, oxo, C1-5 alkylS(O)$_m$—, or amino optionally mono- or di-substituted by $C_{1-5}$ alkyl, phenyl or phenyl $C_{1-5}$ alkyl;
if $Ar_1$ is (ii) then:
  $R^{1'}$ is chosen from H, $C_{1-6}$ alkyl, $C_{1-5}$ alkylS(O)$_m$—, $C_{1-5}$ alkoxyl $C_{1-5}$ alkylthiol , $NH_2$—C(O)—(CH$_2$)$_n$—, heterocycle, heterocycle$C_{1-6}$ alkyl, heteroaryl, or nitrile, each of the aforementioned where possible are optionally partially or fully halogenated or are optionally further substituted with alkylsulfonylamino, alkoxyl, amino, alkylamino, dialkylamino, hydroxyl, oxo, nitro, and nitrile;
  $R_2'$ is chosen from $C_{1-5}$ alkylS(O)$_m$—, J-O—C(O)—O—, $C_{1-5}$ alkyl, $C_{1-5}$ alkoxy;
or if $Ar_1$ is (iii) then:
  ring d is a 5-6 membered heterocyclic ring.
3. The compound according to claim 2 and wherein
if $Ar_1$ is (i) then:
  $R_1$ is chosen from hydrogen, $C_{1-6}$ alkyl or nitrile;
  $R_2$ is chosen from hydrogen, halogen, $C_{1-5}$ alkyl, $C_{1-5}$ alkoxy, oxo or $C_{1-5}$ alkylS(O)$_m$—;
if $Ar_1$ is (ii) then:
  $R^{1'}$ is chosen from H, $C_{1-6}$ alkyl, $C_{1-5}$ alkylS(O)$_m$—, $C_{1-5}$ alkoxyl $C_{1-5}$ alkylthiol , $NH_2$—C(O)—(CH$_2$)$_n$—, morpholino $C_{1-6}$ alkyl, heteroaryl chosen from pyrazole, triazole, imidazole and tetrazole, and nitrile;
  $R_2'$, is chosen from $C_{1-5}$ alkylS(O)$_m$—, J-O—C(O)—O—, $C_{1-5}$ alkyl, $C_{1-5}$ alkoxy;
or if $Ar_1$ is (iii) then:
  ring d is a 5-6 membered heterocyclic ring such that rings c and d fuse to form the following:

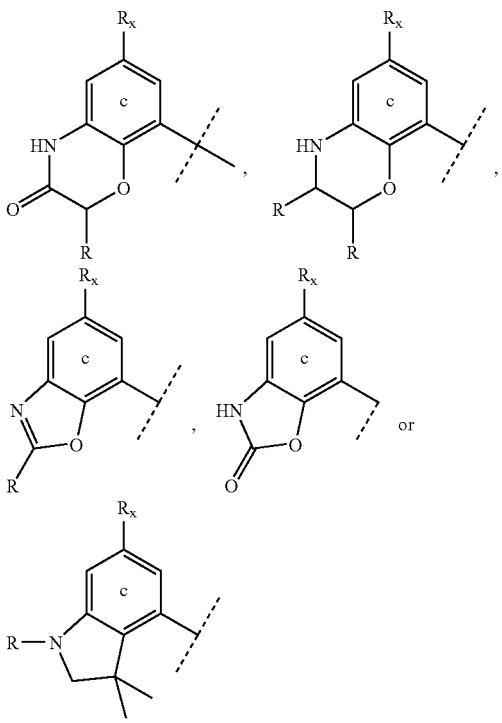

where R is H or $C_{1-3}$ alkyl.

4. The compound according to claim 3 wherein

J is chosen from C1-10 alkyl, aryl or C3-7 cycloalkyl each optionally substituted by $R^b$;

$R_x$ is independently chosen from C1-6 alkyl which may optionally be partially or fully halogenated, acetyl, aroyl, C1-4 alkoxy, which may optionally be partially or fully halogenated, halogen, methoxycarbonyl, phenylsulfonyl and —$SO_2$—$CF_3$;

r is 1-4;

$R^a$ and $R^b$ are each independently chosen from hydrogen, C1-5 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, C1-5 sulphonylamino, hydroxy, halogen, trifluoromethyl, nitro, nitrile or $R^a$ and $R^b$ are chosen from; heterocycle is chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl is chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl;

$R_7$ is hydrogen;

and X is O.

5. The compound according to claim 4 wherein $R_5$ is: —O—, —S—, —NH—, C(O), a linear chain chosen from —NH(CR_7R_8)_r—, —(CR_7R_8)_r—, —O(CR_7R_8)_r—, C(O)—O(CR_7R_8)_r—, S(CR_7R_8)_r—, C(O)(CR_7R_8)_r— and —C(O)NH(CR_7R_8)_r—, wherein r is 1-3 and each of the aforementioned $R_5$ is further substituted by $R^a$.

6. The compound according to claim 5 wherein

J is C1-10 alkyl;

$R_x$ is independently chosen from C1-6 alkyl which may optionally be partially or fully halogenated and C1-3 alkoxy, which may optionally be partially or fully halogenated;

$R_3$ and $R_4$ are each independently chosen from hydrogen, C1-3 alkyl and chloro;

$R_6$ is chosen from hydrogen and amino;

$R_5$ is: —NH—, C(O), a linear chain chosen from —NH(CR_7R_8)_r—, —(CR_7R_8)_r—, —O(CR_7R_8)_r—, —C(O)—O(CR_7R_8)_r—, C(O)(CR_7R_8)_r— and —C(O)NH(CR_7R_8)_r— wherein r is 1-2 and each of the aforementioned $R_5$ is further substituted by $R^a$, $R^a$ and $R^b$ are each independently chosen from hydrogen, C1-5 alkyl, C3-7 cycloalkylC0-2 alkyl, aryl, C1-5 alkoxy, amino, C1-5 alkylamino, C1-3 dialkylamino, C1-3 acyl, C1-5 alkoxycarbonyl, C1-3 acyloxy, C1-3 acylamino, C1-3 sulphonylamino, hydroxy, halogen, trifluoromethyl, nitro, nitrile;

or $R^a$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl.

7. The compound according to claim 6 wherein

J is C1-5 alkyl;

$R_x$ is independently chosen from C1-5 alkyl which may optionally be partially or fully halogenated and C1-2 alkoxy, which may optionally be partially or fully halogenated;

$R_3$ is hydrogen;

$R_4$ is chosen from hydrogen and methyl;

$R_8$ is hydrogen, methyl, ethyl, $CH_2OH$ and $CH_2OCH_3$.

8. The compound according to claim 7 wherein $R_3$ is hydrogen;

$R_4$ is methyl;

$R^a$ is chosen from hydrogen, C1-5 alkyl, C3-6 cycloalkylC0-2 alkyl, phenyl, C1-5 alkoxy, amino, C1-5 alkylamino, C1-3 dialkylamino, C1-3 acyl, C1-5 alkoxycarbonyl, C1-3 acyloxy, C1-3 acylamino, hydroxy, halogen;

or $R^a$ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl.

9. The compound according to claim 8 wherein $R^a$ is chosen from hydrogen, C1-5 alkyl, C3-6 cycloalikyl, phenyl, C1-5 alkoxy, C1-5 alkoxycarbonyl, C1-3 acyloxy, C1-3 acylamino, hydroxy, halogen;

or $R^a$ is chosen from morpholinyl, piperidinyl and pyridinyl.

10. The compound according to claim 9 wherein $R_5$ is —NH(CR_7R_8)_r—$R^a$, wherein $R^a$ is chosen from phenyl, morpholinyl, piperidinyl, pyridinyl, cyclopropyl, cyclohexyl, C1-5 alkyl and C1-3 alkoxy.

11. The compound according to claim 10 wherein Ar₁ is
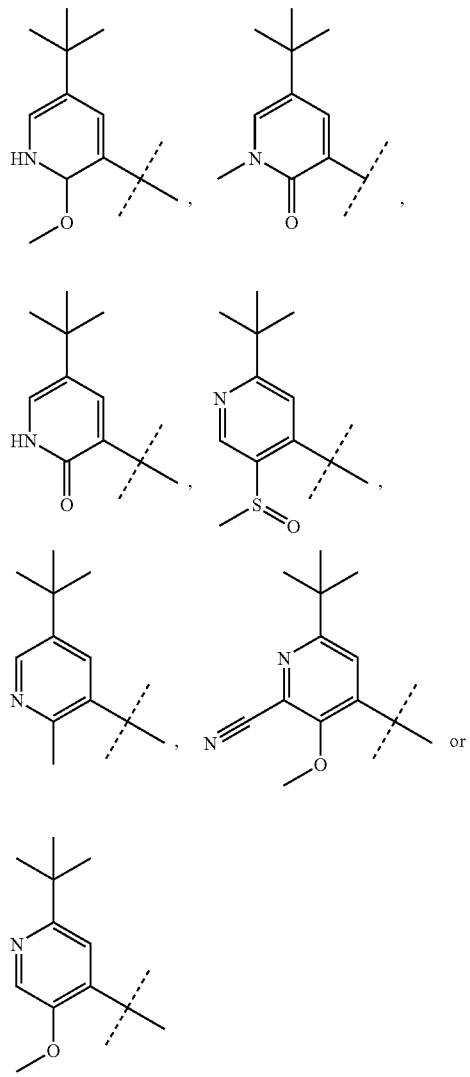
or Ar₁ is:
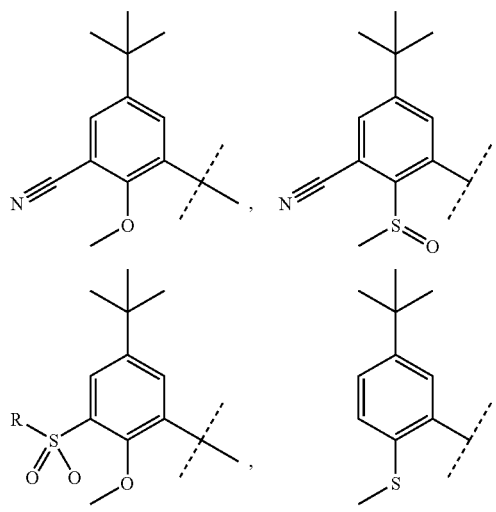
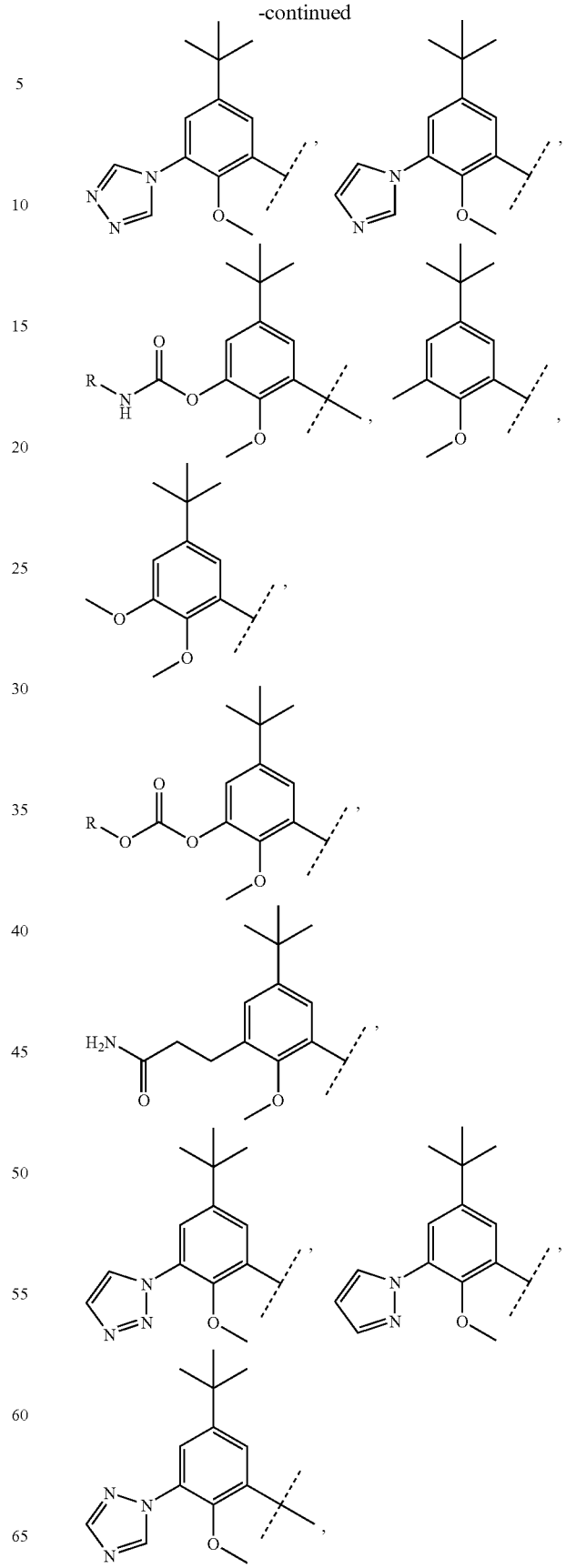

-continued

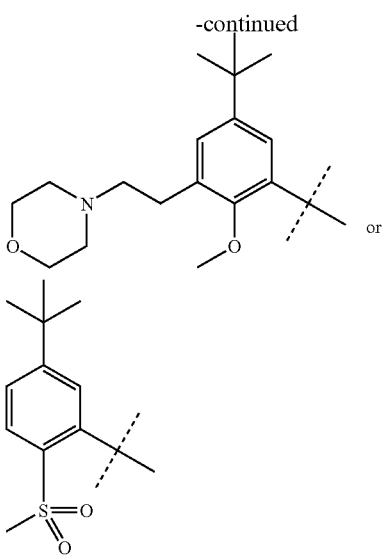

wherein R is H or C1-3 alkyl.

12. A compound chosen from:
1-[5-(5-tert-Butyl-2-methoxy-3-methylsulfamoyl-phenylcarbamoyl)-2-methyl-phenyl]-1H-1,2,3-triazole-4-carboxylic acid (2,2-dimethyl-propyl)-amide;
1-[5-(5-tert-Butyl-3-1,3-dioxolan-2-yl-2-methoxy-phenylcarbamoyl)-2-methyl-phenyl]-1H-1,2,3-triazole-4-carboxylic acid (2,2-dimethyl-propyl)-amide;
1-[5-(5-tert-Butyl--dimethylaminomethyl-2-methoxy-phenylcarbamoyl)-2-methyl-phenyl]-1H-1,2,3-triazole-4-carboxylic acid (2,2-dimethyl-propyl)-amide;
1-{5-[5-tert-Butyl-2-methoxy-3-(4-methyl-piperazin-1-ylmethyl)-phenylcarbamoyl]-2-methyl-phenyl}-1H-1,2,3-triazole-4-carboxylic acid (2,2-dimethyl-propyl)-amide;
1-{5-[5-tert-Butyl-3-((S)-3-dimethylamino-pyrrolidin-1-ylmethyl)-2-methoxy-phenylcarbamoyl]-2-methyl-phenyl}-1H-1,2,3-triazole-4-carboxylic acid (2,2-dimethyl-propyl)-amide;
1-[5-(5-tert-Butyl-2-methoxy-3-morpholin-4-ylmethyl-phenylcarbamoyl)-2-methyl-phenyl]-1H-1,2,3-triazole-4-carboxylic acid (2,2-dimethyl-propyl)-amide;
1-{5-[5-tert-Butyl-3-(2-dimethylamino-ethylcarbamoyl)-2-methoxy-phenylcarbamoyl]-2-methyl-phenyl}-1H-1,2,3-triazole-4-carboxylic acid (2,2-dimethyl-propyl)-amide;
1-[5-(5-tert-Butyl-3-{[(2-dimethylamino-ethyl)-methyl-amino]-methyl}-2-methoxy-phenylcarbamoyl)-2-methyl-phenyl]-1H-1,2,3-triazole-4-carboxylic acid (2,2-dimethyl-propyl)-amide;
1-[5-(5-tert-Butyl-3-{[(2-dimethylamino-ethyl)-methyl-amino]-methyl}-2-methoxy-phenylcarbamoyl)-2-methyl-phenyl]-1H-1,2,3-triazole-4-carboxylic acid ((R)-1-phenyl-ethyl)-amide;
1-[5-(2-tert-Butyl-5-methoxy-pyridin-4-ylcarbamoyl)-2-methyl-phenyl]-1H-1,2,3-triazole-4-carboxylic acid (2,2-dimethyl-propyl)-amide and
1-[5-(5-tert-Butyl-2-methanesulfinyl-phenylcarbamoyl)-2-methyl-phenyl]-1H-1,2,3-triazole-4-carboxylic acid (2,2-dimethyl-propyl)-amide or
a pharmaceutically acceptable salt, acid, ester or isomer thereof.

13. A compound chosen from 1-[5-(5-tert-Butyl-3-cyano-2-methoxy-phenylcarbamoyl)-2-methyl-phenyl]-1H-[1,2,3]triazole-4-carboxylic acid (2,2-dimethyl-propyl)-amide;
1-[5-(5-tert-Butyl-3-cyano-2-methanesulfinyl-phenylcarbamoyl)-2-methyl-phenyl]-H-[1,2,3]triazole-4-carboxylic acid (2,2-dimethyl-propyl)-amide;
1-[5-(6-tert-Butyl-2-cyano-3-methoxy-pyridin-4-ylcarbamoyl)-2-methyl-phenyl]-1H-[1,2,3]triazole-4-carboxylic acid (2,2-dimethyl-propyl)-amide;
1-[5-(5-tert-Butyl-2-methoxy-3-trifluoromethanesulfonyl-phenylcarbamoyl)-2-methyl-phenyl]-1H-[1,2,3]triazole-4-carboxylic acid (2,2-dimethyl-propyl)-amide;
1-[5-(5-tert-Butyl-3-methanesulfinyl-2-methoxy-phenylcarbamoyl)-2-methyl-phenyl]-1H-[1,2,3]triazole-4-carboxylic acid (2,2-dimethyl-propyl)-amide;
1-[5-(5-tert-butyl-2-methyl-pyridin-3-ylcarbamoyl)-2-methyl-phenyl]-1H-[1,2,3]triazole-4-carboxylic acid (2,2-dimethyl-propyl)-amide;
1-[5-(2-tert-Butyl-5-methanesulfinyl-pyridin-4-ylcarbamoyl)-2-methyl-phenyl]-1H-[1,2,3]triazole-4-carboxylic acid (2,2-dimethyl-propyl)-amide;
1-[5-(6-tert-Butyl-3-oxo-3,4-dihydro-2H-benzo[1,4]oxazin-8-ylcarbamoyl)-2-methyl-phenyl]-1H-[1,2,3]triazole-4-carboxylic acid (2,2-dimethyl-propyl)-amide;
1-[5-(5-tert-Butyl-2-methyl-benzooxazol-7-ylcarbamoyl)-2-methyl-phenyl]-1H-[1,2,3]triazole-4-carboxylic acid (2,2-dimethyl-propyl)-amide;
1-[5-(6-tert-Butyl-3,4-dihydro-2H-benzo[1,4]oxazin-8-ylcarbamoyl)-2-methyl-phenyl]-1H-[1,2,3]triazole-4-carboxylic acid (2,2-dimethyl-propyl)-amide;
1-[5-(5-tert-Butyl-2-oxo-2,3-dihydro-benzooxazol-7-ylcarbamoyl)-2-methyl-phenyl]-1H-[1,2,3]triazole-4-carboxylic acid (2,2-dimethyl-propyl)-amide;
1-[5-(5-tert-Butyl-2,2-dimethyl-3-oxo-2,3-dihydro-benzofuran-7-ylcarbamoyl)-2-methyl-phenyl]-1H-[1,2,3]triazole-4-carboxylic acid (2,2-dimethyl-propyl)-amide;
1-[5-(5-tert-Butyl-2-methylsulfanyl-phenylcarbamoyl)-2-methyl-phenyl]-1H-[1,2,3]triazole-4-carboxylic acid (2,2-dimethyl-propyl)-amide;
1-[5-(5-tert-Butyl-2-methanesulfonyl-phenylcarbamoyl)-2-methyl-phenyl]-1H-[1,2,3]triazole-4-carboxylic acid (2,2-dimethyl-propyl)-amide;
1-[5-(5-tert-Butyl-2-oxo-1,2-dihydro-pyridin-3-ylcarbamoyl)-2-methyl-phenyl]-1H-[1,2,3]triazole-4-carboxylic acid (2,2-dimethyl-propyl)-amide;
1-[5-(5-tert-Butyl-1-methyl-2-oxo-1,2-dihydro-pyridin-3-ylcarbamoyl)-2-methyl-phenyl]-1H-[1,2,3]triazole-4-carboxylic acid (2,2-dimethyl-propyl)-amide;
1-{5-[5-tert-Butyl-1-(2-morpholin-4-yl-ethyl)-2-oxo-1,2-dihydro-pyridin-3-ylcarbamoyl]-2-methyl-phenyl}-1H-[1,2,3]triazole-4-carboxylic acid (2,2-dimethyl-propyl)-amide;
1-[5-(5-tert-Butyl-2-methoxy-pyridin-3-ylcarbamoyl)-2-methyl-phenyl]-1H-[1,2,3]triazole-4-carboxylic acid (2,2-dimethyl-propyl)-amide;
1-[5-(5-tert-Butyl-2-methoxy-3-[1,2,3]triazol-1-yl-phenylcarbamoyl)-2-methyl-phenyl]-1H-[1,2,3]triazole-4-carboxylic acid (2,2-dimethyl-propyl)-amide;
1-[5-(5-tert-Butyl-2-methoxy-3-pyrazol-1-yl-phenylcarbamoyl)-2-methyl-phenyl]-1H-[1,2,3]triazole-4-carboxylic acid (2,2-dimethyl-propyl)-amide;
1-[5-(5-tert-Butyl-2-methoxy-3-[1,2,4]triazol-1-yl-phenylcarbamoyl)-2-methyl-phenyl]-1H-[1,2,3]triazole-4-carboxylic acid (2,2-dimethyl-propyl)-amide;

1-[5-(5-tert-Butyl-2-methoxy-3-[1,2,4]triazol-4-yl-phenylcarbamoyl)-2-methyl-phenyl]-1H-[1,2,3]triazole-4-carboxylic acid (2,2-dimethyl-propyl)-amide;

1-[5-(5-tert-Butyl-3-imidazol-1-yl-2-methoxy-phenylcarbamoyl)-2-methyl-phenyl]-1H-[1,2,3]triazole-4-carboxylic acid (2,2-dimethyl-propyl)-amide;

1-[5-(5-tert-Butyl-2,3-dimethoxy-phenylcarbamoyl)-2-methyl-phenyl]-1H-[1,2,3]triazole-4-carboxylic acid (2,2-dimethyl-propyl)-amide;

Carbonic acid 5-tert-butyl-3-{3-[4-(2,2-dimethyl-propylcarbamoyl)-[1,2,3]triazol-1-yl]-4-methyl-benzoylamino}-2-methoxy-phenyl ester ethyl ester;

Methyl-carbamic acid 5-tert-butyl-3-{3-[4-(2,2-dimethyl-propylcarbamoyl)-[1,2,3]triazol-1-yl-4-methyl-benzoylamino}-2-methoxy-phenyl ester;

1-[5-(5-tert-Butyl-2-methoxy-3-methyl-phenylcarbamoyl)-2-methyl-phenyl]-1H-[1,2,3]triazole-4-carboxylic acid (2,2-dimethyl-propyl)-amide;

1-[5-(1-Acetyl-6-methoxy-3,3-dimethyl-2,3-dihydro-1H-indol-5-ylcarbamoyl)-2-methyl-phenyl]-1H-[1,2,3]triazole-4-carboxylic acid (2,2-dimethyl-propyl)-amide;

1-{5-[5-tert-Butyl-3-(2-carbamoyl-ethyl)-2-methoxyphenylcarbamoyl]-2-methyl-phenyl}-1H-[1,2,3]triazole-4-carboxylic acid (2,2-dimethyl-propyl)-amide;

1-{-5-[5-tert-Butyl-2-methoxy-3-(2-morpholin-4-yl-ethyl)-phenylcarbamoyl]-2-methyl-phenyl}-1H-[1,2,3]triazole-4-carboxylic acid (2,2-dimethyl-propyl)-amide and 1-[5-(5-tert-Butyl-3-carbamoyl-2-methoxy-phenylcarbamoyl)-2-methyl-phenyl]-1H-[1,2,3]triazole-4-carboxylic acid (2,2-dimethyl-propyl)-amide or a pharmaceutically acceptable salt, acid, ester or isomer thereof.

14. A pharmaceutical composition containing a pharmaceutically effective amount of a compound according to claim 1 and one or more pharmaceutically acceptable carriers and/or adjuvants.

15. A method of treating a disease or condition chosen from osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus, insulin-dependent diabetes mellitus, rheumatoid arthritis, toxic shock syndrome, Alzheimer's disease, diabetes, inflammatory bowel diseases, acute and chronic pain, stroke, myocardial infarction alone or following thrombolytic therapy, thermal injury, adult respiratory distress syndrome (ARDS), multiple organ injury secondary to trauma, acute glomerulonephritis, dermatoses with acute inflammatory components, acute purulent meningitis, syndromes associated with hemodialysis, leukopherisis, granulocyte transfusion associated syndromes, necrotizing entrerocolitis, restenosis following percutaneous transluminal coronary angioplasty, traumatic arthritis, sepsis, chronic obstructive pulmonary disease and congestive heart failure, said method comprising administering to a patient a pharmaceutically effective amount of a compound according to claim 1.

* * * * *